(12) United States Patent
Nishida et al.

(10) Patent No.: US 12,035,973 B2
(45) Date of Patent: Jul. 16, 2024

(54) METHOD FOR DETECTING STRESSED STATE AND STRESS DETECTION APPARATUS

(71) Applicant: OSAKA UNIVERSITY, Osaka (JP)

(72) Inventors: Kohji Nishida, Osaka (JP); Kazuichi Maruyama, Osaka (JP); Noriyasu Hashida, Osaka (JP); Reiko Kobayashi, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 1029 days.

(21) Appl. No.: 16/964,029

(22) PCT Filed: Jan. 25, 2019

(86) PCT No.: PCT/JP2019/002394
§ 371 (c)(1),
(2) Date: Jul. 22, 2020

(87) PCT Pub. No.: WO2019/146738
PCT Pub. Date: Aug. 1, 2019

(65) Prior Publication Data
US 2021/0038077 A1    Feb. 11, 2021

(30) Foreign Application Priority Data

Jan. 25, 2018  (JP) ................. 2018-010822

(51) Int. Cl.
*A61B 3/14*    (2006.01)
*A61B 3/10*    (2006.01)
*A61B 5/16*    (2006.01)

(52) U.S. Cl.
CPC ............. *A61B 3/14* (2013.01); *A61B 3/102* (2013.01); *A61B 5/165* (2013.01)

(58) Field of Classification Search
CPC .......... A61B 3/14; A61B 3/102; A61B 5/165; A61B 5/0066; A61B 3/1225; A61B 5/0073
(Continued)

(56) References Cited

U.S. PATENT DOCUMENTS

2013/0058553 A1    3/2013   Yonezawa et al.

FOREIGN PATENT DOCUMENTS

| CA | 2 373 178 A1 | 11/2000 |
| JP | 2000-275248 A | 10/2000 |

(Continued)

OTHER PUBLICATIONS

Koji et al., machine translation of JP-2014104275 (Year: 2014).*
(Continued)

*Primary Examiner* — Balram T Parbadia
*Assistant Examiner* — Rahman Abdur
(74) *Attorney, Agent, or Firm* — Dilworth & Barrese, LLP

(57) ABSTRACT

A method for detecting a stressed state, including a step of detecting a stressed state of a subject based on a tomographic image of a choroid of the subject, and a stress detection apparatus including: an image acquisition unit that acquires a tomographic image of a choroid of a subject; a calculation unit that calculates a choroidal thickness or a volume of the choroid based on the tomographic image; and a detection unit that detects a stressed state of the subject based on the choroidal thickness or the volume of the choroid.

7 Claims, 10 Drawing Sheets

(58) Field of Classification Search
USPC .......................................................... 351/206
See application file for complete search history.

(56) References Cited

FOREIGN PATENT DOCUMENTS

| JP | 2002-544159 | A | | 12/2002 | |
|---|---|---|---|---|---|
| JP | 2007-225606 | A | | 9/2007 | |
| JP | 2008-212179 | A | | 9/2008 | |
| JP | 2010-246787 | A | | 11/2010 | |
| JP | 2012-251857 | A | | 12/2012 | |
| JP | 2013-66702 | A | | 4/2013 | |
| JP | 2014-104275 | A | | 6/2014 | |
| JP | 2017-74273 | A | | 4/2017 | |
| JP | 2017-169974 | A | | 9/2017 | |
| WO | 2015/188279 | A1 | | 12/2015 | |
| WO | WO-2015188279 | A1 | * | 12/2015 | ............. A61B 3/102 |

OTHER PUBLICATIONS

Ikuno et al. "Choroidal Thickness in Healthy Japanese Subjects", Investigative Ophthalmology & Visual Science (Year: 2010).*
Demirok et al. Choroidal and Ganglion Cell Complex Thicknesses in Subjects with Type A Behavior Pattern: An Optical Coherence Tomography Study; Journal of Clinical and Analytical Medicine; Ankara, Turkey; (Year: 2015).*
Bruno Lumbroso, Choroid Study Defines Normal Ranges of Variation, Retina Today, Apr. 2012 (Year: 2012).*
Manjunath et al. Choroidal Thickness in Normal Eyes Measured Using Cirrus-HD, Optical Coherence Tomography, National Institute of Health Public Access; Sep. 2010. (Year: 2010).*
Kong et al. Measurable Range of Subfoveal Choroidal Thickness with Conventional Spectral Domain Optical Coherence Tomography, Translational Vision Science Technology, Oct. 2018 (Year: 2018).*
Jirarattanasopa et al "Choroidal Thickness, Vascular Hyperpermeability, and Complement Factor H in Age-Related Macular Degeneration and Polypoidal Choroidal Vasculopathy," Investigative Ophthamology & Visual Science, Jun. 2012, vol. 53, No. 7, pp. 3663-3672.
Extended European Search Report from European Patent Application No. 19743747.8 dated Sep. 30, 2021.
Tak et al, "Evaluation of thickness of retnal nerve fiber layer, ganglion cell layer, and choroidal thickness in essential: can eyes be a clue for neurodegeneration?," Acta. Neurol. Belg (2018) 118:235-241.
Maul et al, "Choroidal Thickness Measured by Spectral Domain Optical Coherence Tomography," Opthamology vol. 118, No. 8, Aug. 2011, pp. 1571-1579.
Hussain et al, "An automated method for choroidal thickness measurement from enhanced Depth Imaging Optical Coherence Tomography images," Computerized Medical Imaging and Graphics 63 (2018), pp. 41-51.
Kilic et al, "Choroidal thickness in psoriasis", Int Ophthalmol (2017) 37:173-177.
Kessler et al., "Short screening scales to monitor population prevalences and trends in non-specific psychological distress"; Psychological Medicine, 2002, 32, 959-976.
"Monitoring of the relationship between the central serosal retinopathy and the stress related factor of UM-CTR clinical test registration information, Jul. 25, 2017, URL,https://upload.umin.ac.jp/cgi - open /bin/ctr/ctr_view.cgi?recptno=R000032453".
Quantitative study of choroidal circulation in Saito Yukiku, Hokkaido University Co., Ltd. (Medicine), Mar. 25, Mar. 2014,, and URL,https://eprints.lib.hokudai.ac.jp/dspace/bitstream/2115/56179/1/Michiyuki_Saito.pdf. 11217.
Office Action dated Feb. 16, 2021 in priority application.

* cited by examiner

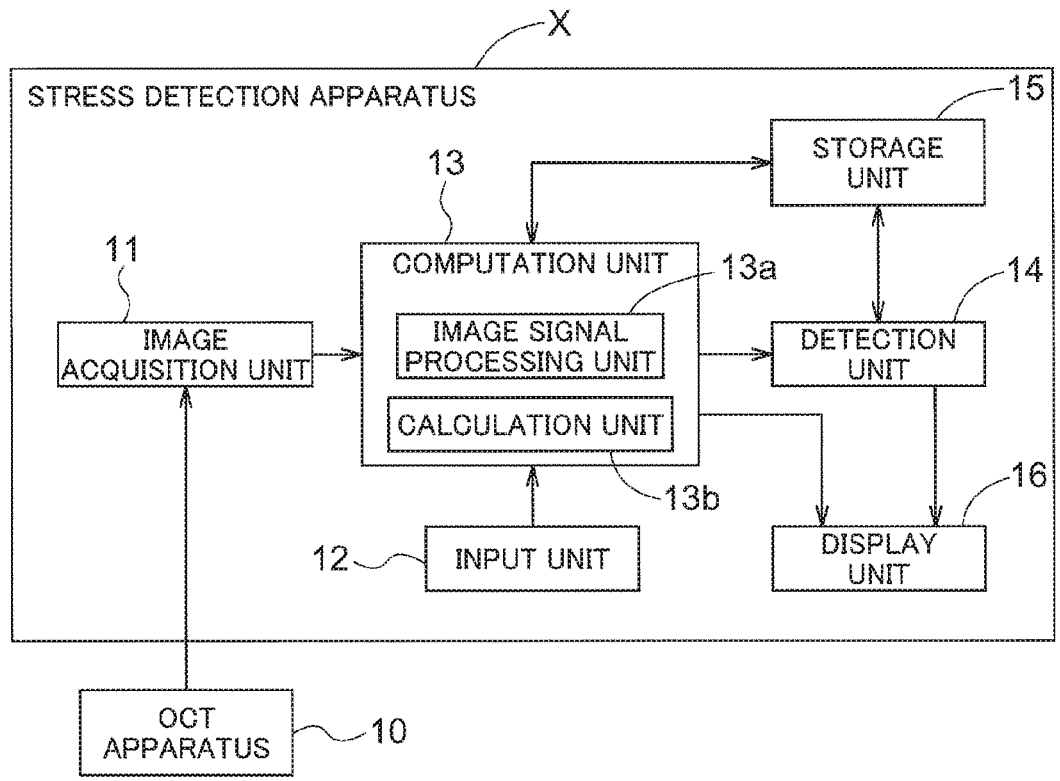
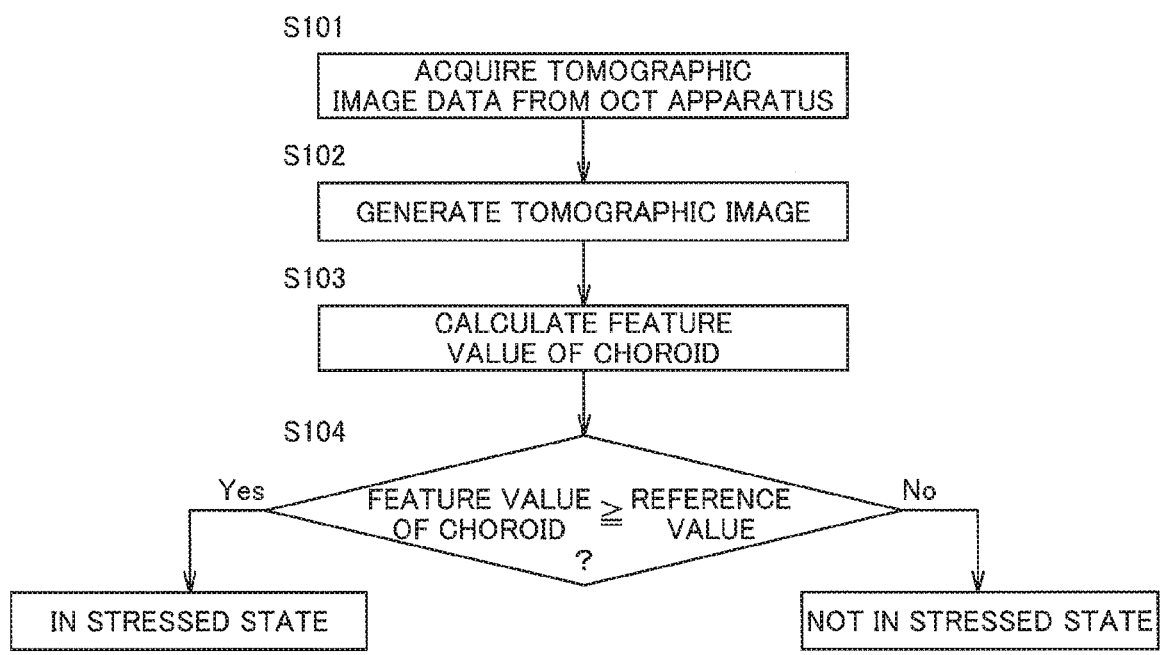

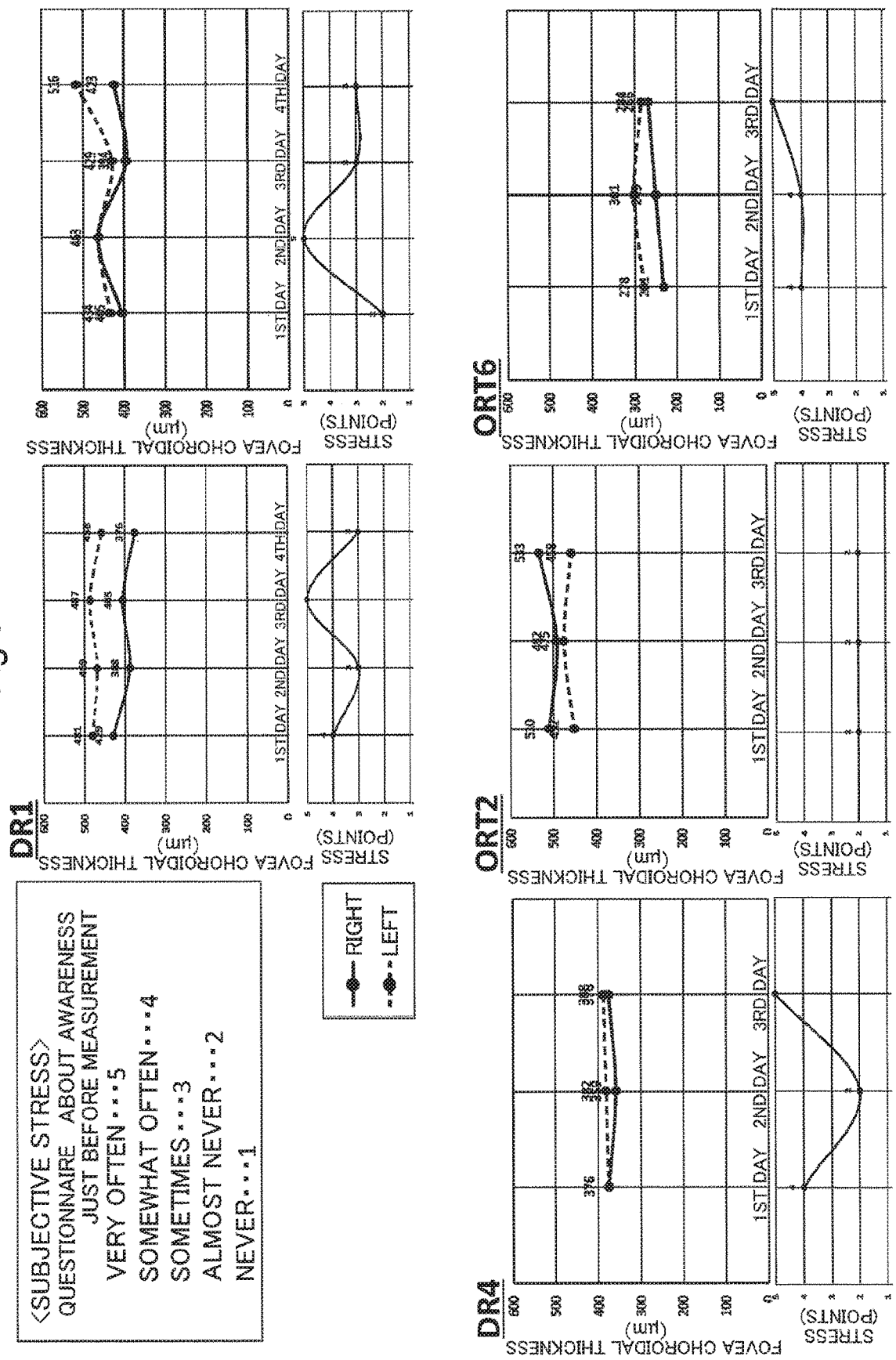

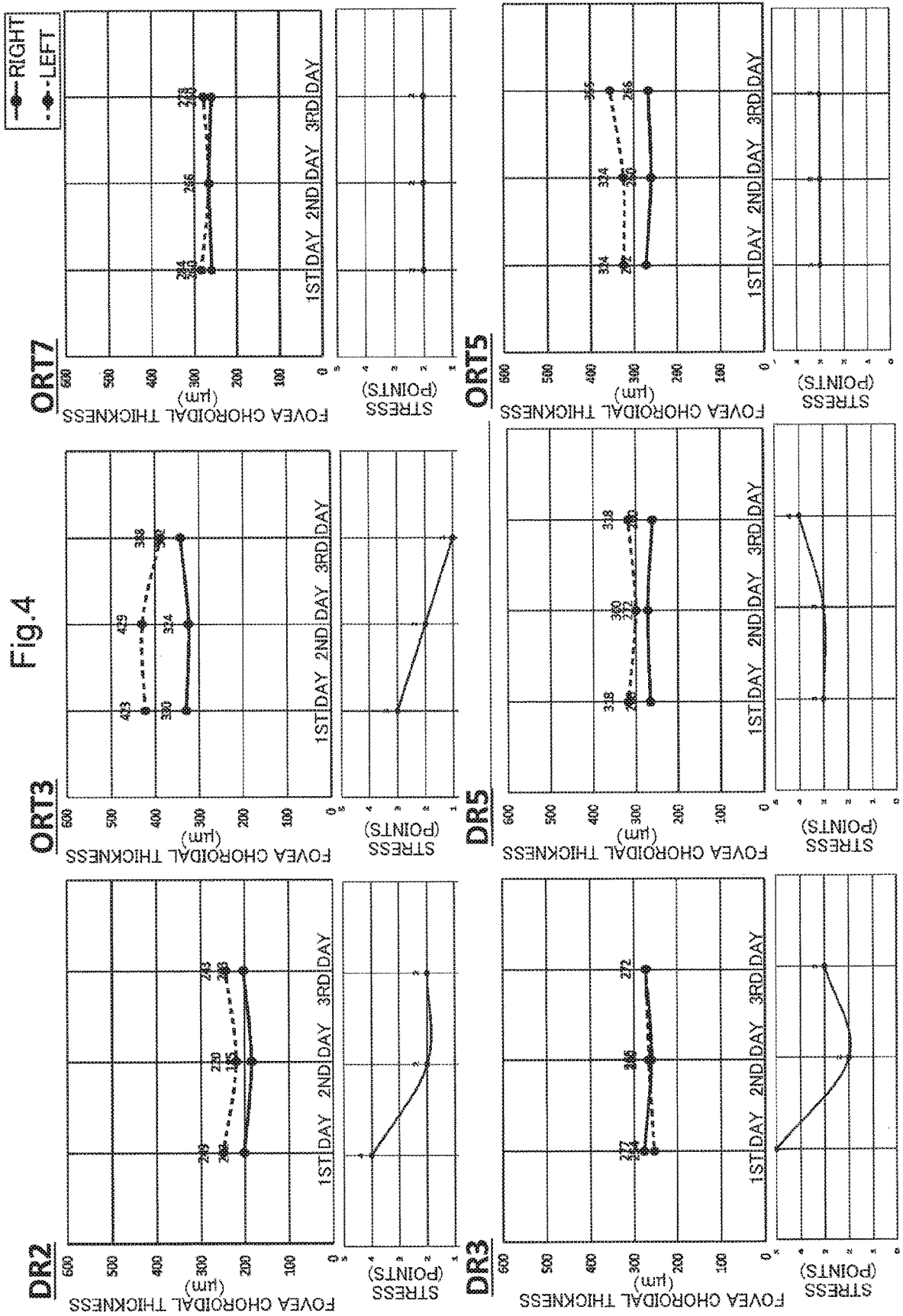

Fig.6

| ID NO. | DR1 | DR2 | DR3 | DR4 | DR5 | ORT1 | ORT2 | ORT3 | ORT5 | ORT6 | ORT7 | DR6 | DR7 | ORT9 |
|---|---|---|---|---|---|---|---|---|---|---|---|---|---|---|
| SEX | FEMALE | MALE | MALE | MALE | MALE | FEMALE | FEMALE | FEMALE | FEMALE | FEMALE | FEMALE | MALE | MALE | FEMALE |
| OCCUPATION | DOCTOR | DOCTOR | DOCTOR | DOCTOR | DOCTOR | ORTHOPTIST | ORTHOPTIST | ORTHOPTIST | ORTHOPTIST | ORTHOPTIST | ORTHOPTIST | DOCTOR | DOCTOR | ORTHOPTIST |
| A. FACTORS THAT MAY CAUSE STRESS | | | | | | | | | | | | | | |
| PSYCHOLOGICAL WORK BURDEN (AMOUNT) | 10 | 9 | 9 | 11 | 10 | 12 | 9 | 8 | 9 | 9 | 8 | 5 | 9 | 10 |
| PSYCHOLOGICAL WORK BURDEN (QUALITY) | 9 | 8 | 9 | 12 | 9 | 12 | 11 | 10 | 9 | 9 | 8 | 6 | 9 | 11 |
| AWARENESS OF PHYSICAL BURDEN | 2 | 2 | 1 | 2 | 3 | 3 | 3 | 2 | 2 | 2 | 1 | 2 | 3 | 4 |
| INTERPERSONAL STRESS AT WORK | 8 | 6 | 11 | 3 | 4 | 10 | 6 | 8 | 7 | 7 | 4 | 6 | 5 | 5 |
| STRESS DUE TO WORK ENVIRONMENT | 1 | 2 | 3 | 1 | 1 | 4 | 2 | 2 | 2 | 1 | 1 | 1 | 1 | 1 |
| WORK CONTROL LEVEL | 8 | 9 | 6 | 6 | 9 | 5 | 8 | 7 | 7 | 9 | 8 | 12 | 9 | 6 |
| SKILL UTILIZATION LEVEL | 4 | 4 | 3 | 3 | 3 | 4 | 3 | 3 | 3 | 3 | 4 | 4 | 3 | 4 |
| WORK APTITUDE LEVEL | 3 | 3 | 2 | 3 | 3 | 3 | 3 | 3 | 3 | 1 | 3 | 4 | 3 | 4 |
| JOB SATISFACTION | 4 | 3 | 3 | 3 | 4 | 4 | 4 | 3 | 3 | 3 | 4 | 4 | 3 | 4 |
| TOTAL SCORE (POINTS) | 49 | 46 | 47 | 44 | 46 | 57 | 49 | 46 | 45 | 44 | 41 | 44 | 45 | 49 |
| B. PSYCHOSOMATIC REACTIONS CAUSED BY STRESS | | | | | | | | | | | | | | |
| LIVELINESS | 4 | 9 | 6 | 6 | 6 | 6 | 7 | 5 | 6 | 4 | 9 | 9 | 9 | 9 |
| IRRITABILITY | 10 | 6 | 6 | 6 | 4 | 9 | 7 | 5 | 7 | 8 | 3 | 3 | 6 | 3 |
| TIREDNESS | 7 | 3 | 7 | 7 | 8 | 6 | 9 | 5 | 6 | 12 | 5 | 3 | 4 | 4 |
| ANXIETY | 10 | 4 | 7 | 8 | 4 | 3 | 9 | 8 | 5 | 8 | 3 | 3 | 5 | 3 |
| DEPRESSION | 17 | 6 | 12 | 11 | 8 | 8 | 13 | 9 | 8 | 22 | 6 | 6 | 6 | 6 |
| PHYSICAL COMPLAINT | 17 | 14 | 16 | 26 | 20 | 19 | 26 | 13 | 17 | 30 | 11 | 11 | 12 | 13 |
| TOTAL SCORE (POINTS) | 65 | 42 | 54 | 64 | 50 | 51 | 71 | 45 | 49 | 84 | 37 | 35 | 42 | 38 |
| C. OTHER FACTORS THAT AFFECT STRESS REACTIONS | | | | | | | | | | | | | | |
| SUPPORT FROM BOSS | 9 | 7 | 6 | 11 | 12 | 8 | 9 | 8 | 10 | 11 | 11 | 11 | 9 | 11 |
| SUPPORT FROM COLLEAGUES | 9 | 7 | 6 | 10 | 12 | 6 | 11 | 9 | 10 | 10 | 11 | 12 | 9 | 12 |
| SUPPORT FROM FAMILY AND FRIENDS | 11 | 11 | 6 | 10 | 12 | 7 | 11 | 11 | 12 | 9 | 11 | 12 | 9 | 12 |
| WORK AND LIFE SATISFACTION | 6 | 6 | 4 | 6 | 8 | 7 | 5 | 5 | 6 | 8 | 6 | 7 | 6 | 7 |
| TOTAL SCORE (POINTS) | 35 | 31 | 22 | 37 | 44 | 28 | 36 | 33 | 38 | 38 | 39 | 42 | 33 | 42 |

Fig. 7
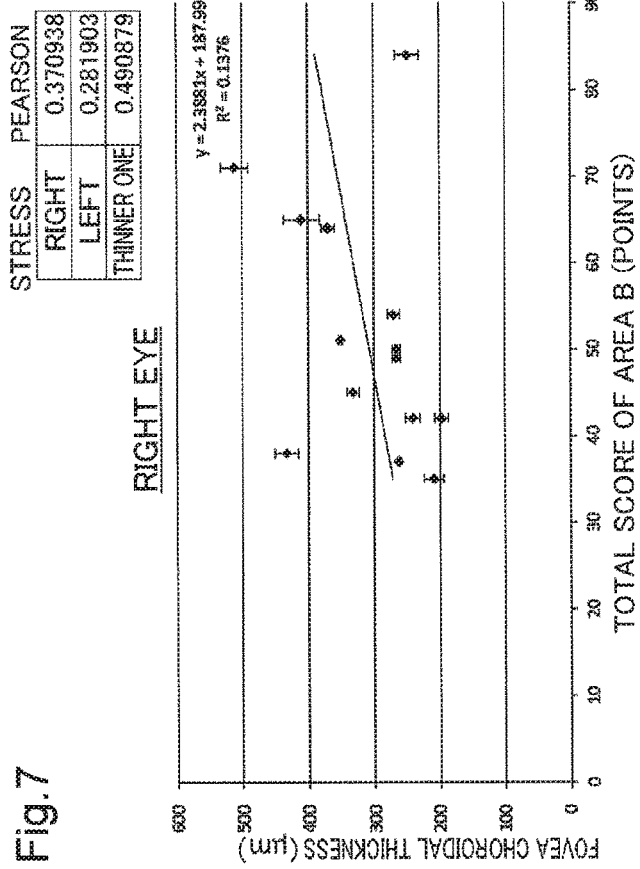
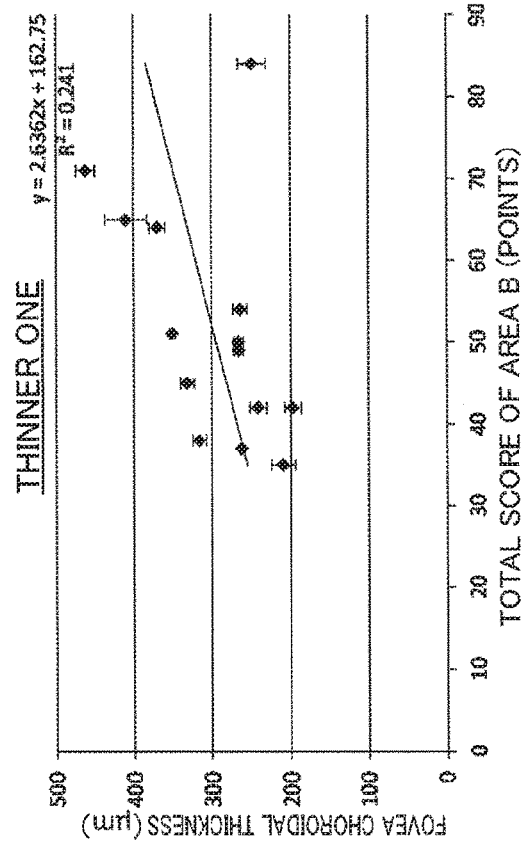

Fig.9

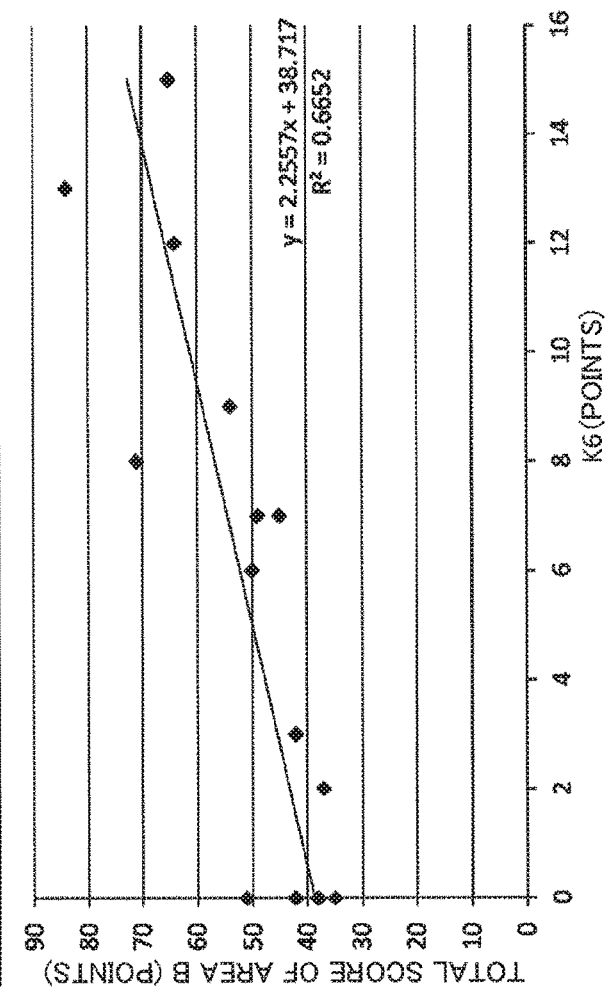

| ID NO. | DR1 | DR2 | DR3 | DR4 | DR5 | ORT1 | ORT2 | ORT3 | ORT4 | ORT5 | ORT6 | DR6 | DR7 | ORT9 |
|---|---|---|---|---|---|---|---|---|---|---|---|---|---|---|
| SEX | FEMALE | MALE | MALE | MALE | MALE | FEMALE | FEMALE | FEMALE | FEMALE | FEMALE | FEMALE | MALE | MALE | FEMALE |
| OCCUPATION | DOCTOR | DOCTOR | DOCTOR | DOCTOR | DOCTOR | ORTHOPTIST | ORTHOPTIST | ORTHOPTIST | ORTHOPTIST | ORTHOPTIST | ORTHOPTIST | DOCTOR | DOCTOR | ORTHOPTIST |
| 1) | 4 | 0 | 2 | 2 | 1 | 0 | 2 | 1 | 1 | 1 | 1 | 1 | 0 | 0 |
| 2) | 2 | 0 | 0 | 2 | 1 | 0 | 0 | 2 | 2 | 0 | 2 | 0 | 1 | 0 |
| 3) | 2 | 0 | 2 | 2 | 1 | 0 | 2 | 1 | 2 | 1 | 1 | 0 | 0 | 0 |
| 4) | 3 | 0 | 1 | 2 | 1 | 0 | 1 | 1 | 1 | 2 | 3 | 0 | 1 | 0 |
| 5) | 2 | 0 | 2 | 2 | 1 | 0 | 1 | 0 | 2 | 2 | 3 | 1 | 0 | 0 |
| 6) | 2 | 0 | 2 | 2 | 1 | 0 | 2 | 2 | 2 | 1 | 3 | 0 | 0 | 0 |
| TOTAL SCORE (POINTS) | 15 | 0 | 9 | 12 | 6 | 0 | 8 | 7 | 10 | 7 | 13 | 2 | 3 | 0 |
| CLASS | SEVERE | NEGATIVE | MODERATE | MODERATE | MILD | NEGATIVE | MILD | MILD | MILD | MILD | SEVERE | NEGATIVE | NEGATIVE | NEGATIVE |

RESULTS 6
CORRELATION BETWEEN SCORE OF
PSYCHOSOMATIC REACTIONS (AREA B)
CAUSED BY STRESS INDICATED BY BRIEF
JOB STRESS QUESTIONNAIRE AND SCORE OF
JAPANESE VERSION OF THE MOOD/ANXIETY
DISORDER QUESTIONNAIRE (K6)

METHOD FOR DETECTING STRESSED STATE AND STRESS DETECTION APPARATUS

TECHNICAL FIELD

The present invention relates to a method for detecting a stressed state and a stress detection apparatus.

BACKGROUND ART

Recently, it has been widely recognized that "stress can lead to various kinds of diseases", that is, stress adversely affects the mind and body and induces various kinds of diseases. Stress refers to a state in which mental and physical disorders occur due to mental and physical burdens caused by various external stimuli. Originally, when animals such as humans feel temporary external stress such as psychosomatic stress, hormones such as cortisol and adrenaline are secreted from the adrenal gland, and an appropriate stimulus is given to the body. The body is strengthened by increasing the heart rate, dilating the heart and blood vessels, increasing the blood glucose level, relaxing the bronchi, and thereby increasing resistance to external stress. However, it is believed that, if the body is exposed to external stress excessively or continuously, the body's defense ability is reduced due to the excessive secretion of hormones, which results in mental or physical abnormalities. The effects of stress on the mind and body differ from person to person, and people with a particularly high stress sensitivity (high-stress people) may have various issues such as school or work absenteeism, which may disturb their daily life. Therefore, it is significantly important to accurately assess a stressed state in order to take care of health, and prevent and treat diseases.

Therefore, in 2015, the Ministry of Health, Labor and Welfare of Japan introduced a stress check system that stipulates examinations to be conducted to understand the degree of psychological burden on workers, face-to-face guidance provided by doctors based on the results of examinations, and so on. In stress check, workers answer questions concerning factors that are considered to be occupational stress, psychosomatic reactions to stress, and other factors that affect stress reactions, and the answers to the questions are converted to scores. The results are aggregated and analyzed for each group of a certain scale, and high-stress people are selected using the scores, based on numerical criteria. However, the stress check is a subjective test in which workers themselves answer questions, and workers may intentionally change answers to pretend that there is no stress. Therefore, there is the possibility of being unable to appropriately select high-stress people. For this reason, it is important to combine subjective examinations with objective examinations in order to select actual high-stress people.

To date, various objective stress tests have been tried. A method in which stress markers such as adrenocortical factors such as cortisol, gonadal factors such as testosterone, locus coeruleus/noradrenaline factors such as amylase, and catecholamine factors such as adrenaline and noradrenaline are employed as indicators has been reported as a method for assessing acute stress reaction (see Patent Document 1). According to the method disclosed in Patent Document 1, instead of blood, saliva, or urine commonly used as a specimen, stress markers in a tissue fluid sampled through a micropore formed in the skin of the subject, using a puncture device or the like, are measured. Also, a method in which apolipoprotein A-II, haptoglobulin, vitamin D binding protein precursor, and the like in serum sampled from a subject are employed as indicators to assess stress has been reported (see Patent Document 2).

Furthermore, a method in which daily changes in cortisol in saliva is employed as an indicator has been reported as a method for assessing chronic stress (see Patent Document 3). According to the method disclosed in Patent Document 3, the standard cortisol concentration change range, obtained from the cortisol concentration in saliva measured in many healthy people over a predetermined time range of the day, is compared with the cortisol concentration change in saliva measured in a specific subject, and people who deviate from the standard cortisol change range are evaluated as people who potentially have chronic stress.

PRIOR ART DOCUMENTS

Patent Documents

Patent Document 1: JP 2012-251857A
Patent Document 2: JP 2007-225606A
Patent Document 3: JP 2000-275248A

SUMMARY OF THE INVENTION

Problems to be Solved by the Invention

However, when blood is used as a specimen as in the method disclosed in Patent Document 2, the act of sampling blood causes mental and physical burdens such as pain, and it may be unable to accurately assess a stressed state due to the load of stress caused by blood sampling. Furthermore, there is a problem in that the act of sampling blood is subjected to restrictions as a medical action, and may induce an infectious disease. The method disclosed in Patent Document 1 aims to reduce the aforementioned burden, but is still invasive and does not completely eliminate the aforementioned burden. When saliva is used as a specimen in the method disclosed in Patent Document 3, the aforementioned burden is reduced. However, as discussed in Patent Document 1, the properties of saliva may change due to external factors such as diet and smoking. In addition, the amount of secretion and composition of saliva significantly differ from person to person. Therefore, it is necessary to set detailed conditions such as the timing of sampling a specimen, and there is a problem in that a complex operation needs to be performed to sample saliva.

The aforementioned stress markers that are constituted by physiochemical substances usually decompose and disappear in a living body in a short time even if they appear in response to stress. For example, the half-life of catecholamine factors such as adrenaline in blood is very short, which is 1 to 2 minutes. Therefore, the measured value may not reflect the stressed state of the living body, and it is difficult to accurately assess the stressed state of the subject. In addition, the concentrations of the physiochemical substances in a living body exhibit large physiological diurnal fluctuations, and also significantly vary from person to person due to differences between sleep-wake rhythms of the individuals. For example, cortisol exhibits diurnal fluctuations in which the value thereof is high in the early morning and low at night, and the value thereof in and after the evening is no higher than half the value in the early morning. Therefore, it is difficult to set constant reference values for the concentrations of the aforementioned physiochemical substances in the living body and simply assess the stressed state. Furthermore, hormones used in the method disclosed in Patent Document 3, such as cortisol, which exhibits large diurnal fluctuations and significantly vary from person to person, cannot be used as stress markers in assessment of chronic stress on the autonomic nervous system, either. Thus, there is no established assessment method at present.

Therefore, there is still a demand for establishing a technique for objectively assess a stressed state of a subject, using stress markers that are capable of accurately reflecting a stressed state of a living body. In particular, there is a demand for establishing a technique for simply and accurately assessing a stressed state of a subject by using a non-invasive means and stress markers that exhibit small diurnal fluctuations or individual differences.

Means for Solving Problems

As a result of conducting constant research to solve the above problems, the inventors have found that it is possible to assess a stressed state of a subject using the choroid, which is a part of the eye tissue, as an indicator. In particular, the inventors have found that the thickness or volume of the choroid accurately reflects a stressed state of the subject. It is possible to objectively detect such changes in the choroid, and it is possible to accurately detect a stressed state of a subject. In addition, by using the optical coherence tomography, it is possible to non-invasively and easily detect a stressed state in a short time.

The inventors have completed the present invention based on these findings.

That is to say, the aspects [1] to [7] shown below of the present invention are provided to solve the above-described problems.

[1] A method for detecting a stressed state, including a step of detecting a stressed state of a subject based on a tomographic image of a choroid of the subject.

With the configuration described in [1] above, it is possible to provide a method for detecting a stressed state with which a stressed state of the subject is detected based on a tomographic image of the choroid, which is a part of the eye tissue of the subject, using the choroid as an indicator. With this configuration, it is possible to objectively detect a stressed state of the subject. Also, since the choroid precisely reflects a stressed state of a living body, it is possible to accurately detect a stressed state of the subject.

Furthermore, it is possible to acquire a tomographic image by using the optical coherence tomography, through which the eye is irradiated with near infrared light, and it is possible to non-invasively and easily detect a stressed state without contact in a short time. Therefore, it is possible to reduce mental and physical burdens on the subject. Therefore, the stress load at the time of detection can be eliminated, and a stressed state of the subject can be accurately detected. Furthermore, there is an advantage in that the influence of the eye movement is small.

Therefore, with the method for detecting a stressed state with this configuration, it is possible to reliably detect a subject in a stressed state. It is possible to recommend a subject detected as being in a stressed state to consult with or take counseling at an appropriate medical institution. In particular, with the method for detecting a stressed state with this configuration, it is possible to detect even a latent stressed state in which stress has not become apparent as a specific symptom, disease, or the like. Therefore, it is possible to detect a stressed state at an early stage, which leads to the prevention of symptoms and diseases caused by stress. Therefore, the method for detecting a stressed state with this configuration can be desirably used for periodical health checkups for workers and the like, which contribute to physical and mental health management of workers, for example. As a result, the method leads to improvement of the working environment, increases work efficiency, and contributes to improvement of labor productivity.

[2] The method for detecting a stressed state according to [1] described above, wherein, in the step of detecting a stressed state, a choroidal thickness is calculated based on the tomographic image, and a stressed state of the subject is detected based on the calculated choroidal thickness.

[3] The method for detecting a stressed state according to [2] described above, wherein a stressed state is detected when the calculated choroidal thickness is no less than 300 μm at a position below a fovea.

With the configuration described in [2] and [3] above, it is possible to provide a method for detecting a stressed state with which a stressed state of the subject is detected based on a tomographic image of the choroid, which is a part of the eye tissue of the subject, using the thickness of the choroid as an indicator. Since the choroidal thickness, which can be explicitly and easily calculated from a tomographic image of the choroid, is used as an indicator of a stressed state, a stressed state of the subject can be more easily and accurately detected.

In particular, with the configuration described in [3] above, a stressed state of the subject can be detected based on a clear reference value, and further improvement in simplicity and accuracy of the detection of a stressed state can be expected.

[4] The method for detecting a stressed state according to [1] described above, wherein, in the step of detecting a stressed state, a volume of the choroid is calculated based on the tomographic image, and a stressed state of the subject is detected based on the calculated volume of the choroid.

With the configuration described in [4] above, it is possible to provide a method for detecting a stressed state with which a stressed state of the subject is detected based on a tomographic image of the choroid, which is a part of the eye tissue of the subject, using the volume of the choroid as an indicator. Since the volume of the choroid, which can be explicitly and easily calculated from a tomographic image of the choroid such as a three-dimensional image, is used as an indicator of a stressed state, a stressed state of the subject can be more easily and accurately detected.

[5] The method for detecting a stressed state according to [2] or [3] described above, wherein the step of detecting a stressed state includes a step of correcting the calculated choroidal thickness based on at least one factor selected from among a detection time, the subject's age, sex, and history of present illness, and an indicator obtained from an eye structure.

With the configuration described in [5] above, it is possible to provide a method for detecting a stressed state that can further accurately detect a stressed state of the subject by correcting the calculated choroidal thickness of the subject based on at least one of the factors that affect the choroidal thickness, selected from among a detection time, the subject's age, sex, and history of present illness, and an indicator obtained from an eye structure, such as an eye axial length or an equivalent spherical area.

[6] The method for detecting a stressed state according to [4] described above, wherein the step of detecting a stressed state includes a step of correcting the calculated volume of the choroid based on at least one factor selected from among a detection time, the subject's age, sex, and history of present illness, and an indicator obtained from an eye structure.

With the configuration described in [6] above, it is possible to provide a method for detecting a stressed state that can further accurately detect a stressed state of the subject by correcting the calculated volume of the choroid of the subject based on at least one of the factors that affect the volume of the choroid, selected from among a detection time, the subject's age, sex, and history of present illness, and an indicator obtained from an eye structure, such as an eye axial length or an equivalent spherical area.

[7] A stress detection apparatus including:
an image acquisition unit that acquires a tomographic image of a choroid of a subject;
a calculation unit that calculates a choroidal thickness or a volume of the choroid based on the tomographic image; and
a detection unit that detects a stressed state of the subject based on the choroidal thickness or the volume of the choroid.

With the configuration described in [7] above, it is possible to provide a stress detection apparatus that detects a stressed state of the subject based on a tomographic image of the choroid, which is a part of the eye tissue of the subject, using the choroidal thickness or the volume of the choroid as an indicator. The stress detection apparatus with this configuration uses the choroidal thickness or the volume of the choroid, which accurately reflects a stressed state of a living body, as an indicator of a stressed state of the subject. Therefore, the stress detection apparatus can reliably detect a stressed state of the subject. Furthermore, by using the optical coherence tomography to acquire a tomographic image of the choroid, it is possible to non-invasively and easily detect a stressed state of the subject without contact in a short time. Therefore, it is possible to reduce mental and physical burdens on the subject. Therefore, the stress load at the time of detection can be eliminated, and a stressed state of the subject can be accurately detected. Also, the stress detection apparatus with this configuration can be desirably used for periodical health checkups for workers and the like. Therefore, by installing the stress detection apparatus in medical examination centers or medical facilities, for example, it is possible to contribute to physical and mental health management of workers.

BRIEF DESCRIPTION OF THE DRAWINGS

FIG. 1 is a block diagram showing an example of a stress detection apparatus according to an embodiment of the present invention.

FIG. 2 is a flowchart showing an example of an operation of the stress detection apparatus according to the embodiment.

FIG. 3 shows results of Example 1 in which a relationship between the choroidal thickness and stress or anxiety was examined, and is a graph showing results of examination of a relationship between the choroidal thickness and subjective stress.

FIG. 4 shows results of Example 1 in which the relationship between the choroidal thickness and stress or anxiety was examined, and is a graph showing results of examination of a relationship between the choroidal thickness and subjective stress.

FIG. 6 shows results of Example 1 in which the relationship between the choroidal thickness and stress or anxiety was examined, and shows the results of the brief job stress questionnaire (57 items) used in an examination of a relationship between the choroidal thickness and the results of the brief job stress questionnaire (57 items).

FIG. 7 shows results of Example 1 in which the relationship between the choroidal thickness and stress or anxiety was examined, and is a graph showing results of examination of a relationship between the choroidal thickness and psychosomatic reactions (B area) caused by the stress indicated by the brief job stress questionnaire (57 items).

FIG. 9 shows results of Example 1 in which the relationship between the choroidal thickness and stress or anxiety was examined, and shows results of the Japanese version of the mood/anxiety disorder questionnaire (K6) used in an examination of a relationship between the choroidal thickness and the results of the Japanese version of the mood/anxiety disorder questionnaire (K6), as well as correlation with psychosomatic reactions (B area) caused by the stress indicated by the brief job stress questionnaire (57 items).

DESCRIPTION OF EMBODIMENTS

Figure 5:
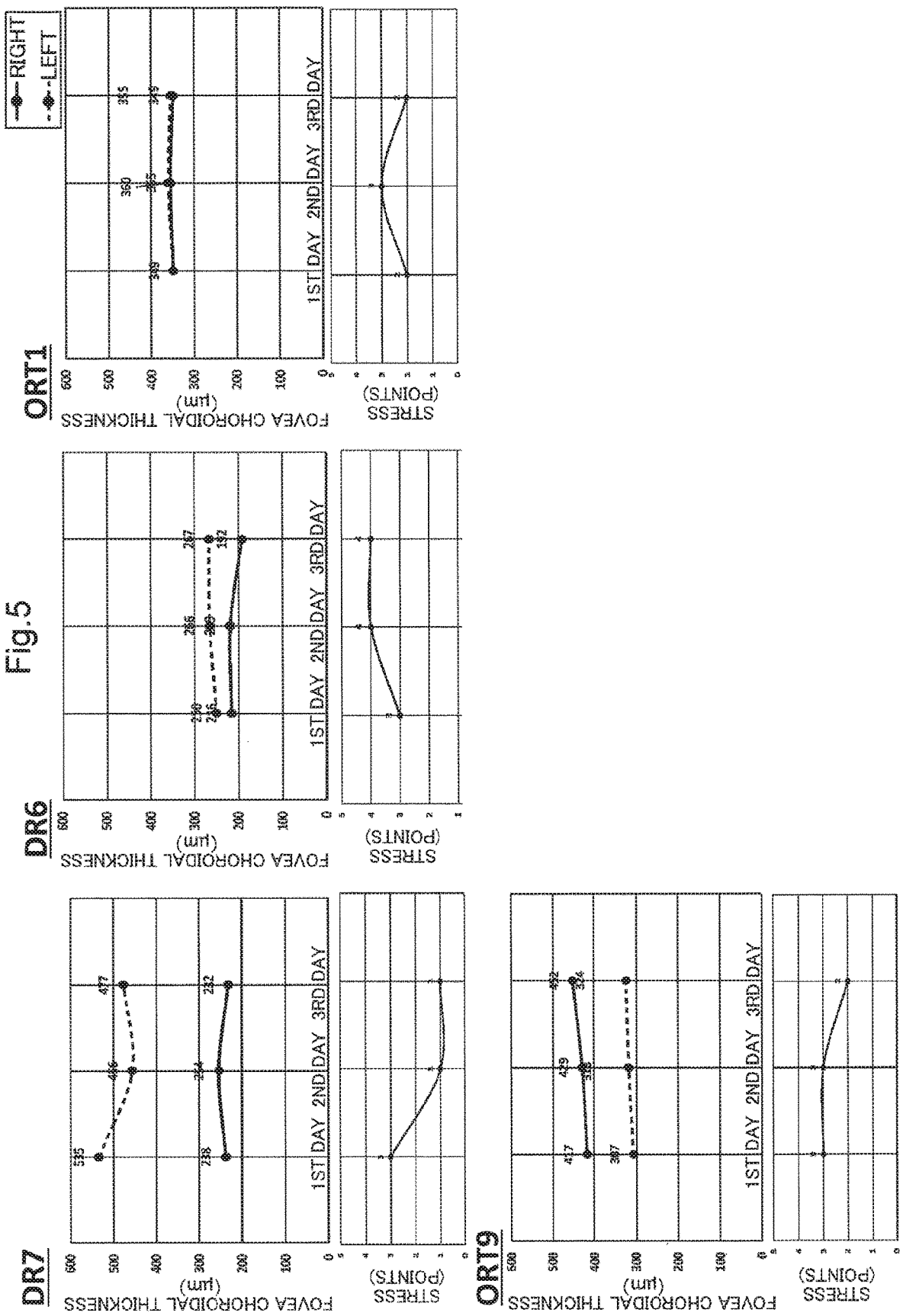
FIG. 5 shows results of Example 1 in which the relationship between the choroidal thickness and stress or anxiety was examined, and is a graph showing results of examination of a relationship between the choroidal thickness and subjective stress.

The following describes a method for detecting a stressed state and a stress detection apparatus according to an embodiment of the present invention in detail. However, note that the present invention is not limited to the embodiment.

Method for Detecting Stressed State

A method for detecting a stressed state according to the present embodiment is a method in which the choroid of the subject is used as an indicator, to detect a stressed state of the subject. In this detection method, the choroid, which is a part of the eye tissue and has not been conventionally recognized as a stress marker, is used as an indicator for a stressed state of the subject.

Examples of the subject of the method for detecting a stressed state according to the present embodiment include animals such as a human, a non-human primate, a rabbit, a rat, a guinea pig, a mouse, a dog, a cat, a cat, a horse, a cow, a pig, a sheep, a goat, a chicken, and so on. However, the subject is especially preferably a human.

A stressed state in the method for detecting a stressed state according to the present embodiment is a tensed state that occurs due to mental and physical burdens caused by various stimuli. Stimuli that induce stress are called stressors, which can be classified into, for example, those caused by environmental factors, those caused by physical factors, those caused by psychological factors, those caused by social factors. Examples of environmental factors include temperature, humidity, light, weather, noise, vibration, exposure to a harmful substance, air pollution, and so on. Examples of physical factors include a trauma, illness, excessive exercise, lack of exercise, physical fatigue, lack of sleep, insufficient nutrition, aging, an unhealthy lifestyle, obesity, and so on. Furthermore, active oxygen species or the like that are excessively generated as a result of the imbalance between the oxidative action of active oxygen and the antioxidative action of an antioxidant or the like in the living body may be included in the physical factors. Examples of psychological factors include anxiety, worry, frustration, anger, fear, disappointment, conflict, and so on. Example of social factors include human relationships, employment, a job change, unemployment, admission into a school, entrance into higher education, poor school performance, bullying, and so on. However, stressors are not limited to these examples.

The stressed state that is to be detected using the method for detecting a stressed state according to the present embodiment is not particularly limited as long as it is a state that is induced by a stressor, and may be a short-term acute stressed state or a long-term chronic stressed state. A stressed state may refer to a stress-related symptom or disease (hereinafter also abbreviated as "a stress symptom" and "a stress disease", respectively), and a latent stressed state in which no psychosomatic symptom or disease has become apparent may also be detected. When a living body is exposed to a stimulus such as a stressor, the autonomic nervous system, the endocrine system, the immune system, and so on interact with each other, and thus the living body maintains its homeostasis. However, when a living body is exposed to a stressor excessively and continuously, the autonomic nervous system is unbalanced, the parasympathetic nerves do not properly function, and the sympathetic nerves continue to be hyperactive. If such a state in which the sympathetic nerves are dominant continues, the living body's resistance to stressors is gradually weakened, and various symptoms and diseases are induced by the functional decline of the autonomic nervous system, the endocrine system, the immune system, and so on. Therefore, a stressed state may preferably refer to a sympathetic dominant state, and symptoms and diseases induced by such a sympathetic dominant state.

Examples of stress symptoms include; physical symptoms such as stiff shoulders, palpitations, dizziness, insomnia, headache, weight fluctuations, decreased appetite, eating disorders, abdominal pain, and addiction; psychological symptoms such as anxiety, anger, impatience, and lethargy; and social symptoms such as overeating, drinking, and withdrawal. Examples of stress diseases include; mental and neurological diseases such as depression, neurosis, and autonomic ataxia; cardiovascular diseases such as hypertension, arteriosclerosis, angina pectoris, and myocardial infarction; endocrine and metabolic disorders such as obesity, diabetes, hyperlipidemia, and hyperthyroidism; respiratory diseases such as secretory bronchitis and a hyperventilation syndrome; gastrointestinal diseases such as irritable bowel syndrome, gastric and duodenal ulcers, ulcerative colitis, and cardiogenic vomiting; skin diseases such as atopic dermatitis, psoriasis, and alopecia areata; ophthalmic diseases such as central serous chorioretinopathy (CSC), eye strain, blepharospasm, and dry eye; ear, nose, and throat diseases such as Meniere's disease; urinary and genital diseases such as nocturia; and inflammatory diseases such as cancer and chronic inflammation. In particular, psychiatric and neurological disorders are envisaged, which include, for example: anxiety disorders that cause suffering and interfere with life due to excessive anxiety and fear, represented by panic disorder, social anxiety disorder, generalized anxiety disorder, phobias, and so on; and mood disorders that cause mood abnormalities, represented by bipolar disorder, depression, dysthymic disorder, and so on. A stressed state causes, for example, exacerbation of various symptoms and diseases, and therefore, the stress symptoms and diseases include not only the onset of various symptoms and diseases, but also the exacerbation thereof.

In the method for detecting a stressed state according to the present embodiment, the choroid, which is an indicator used to detect a stressed state, is a tissue that includes a large number of pigment cells and blood vessels between the retina and the sclera. From a histological point of view, the choroid can be divided into four layers, namely, from the retina side, the basal plate (Bruch's membrane), the choriocapillaris plate, the vascular plate, and the suprachoroidal plate. The choroid is a tissue mostly constituted by blood vessels, and it has been reported that the amount of blood flow in the choroid reaches 85% of the total amount of ocular blood flow (for example, see Experimental Eye Research, 15(1), 1973, p 15-29). Therefore, it can be derived that the choroid is strongly affected by physiochemical substances. In addition, it has been reported that the choroidal blood vessels have low autoregulatory abilities unlike the retinal blood vessels, and that the amount of blood flowing through the choroidal blood vessels changes due to various physiological stimuli such as blood pressure (see Arch Ophthalmol, 83(1), 1970, p 95-99, for example). Therefore, the choroidal blood vessels are strongly affected by changes in the general condition of the living body. Furthermore, it is known that receptors that affect the tension of blood vessels are developed in the choroidal blood vessels, and it is known that the amount of blood flow in the choroid changes especially in the case of the pregnancy hypertension syndrome.

The method for detecting a stressed state according to the present embodiment uses the choroid, which is a part of the eye tissue as described above, as an indicator of a stressed state. It is envisaged that the choroid can reflect changes in the blood vessels throughout the body, and accurately reflect a stressed state of the living body. Meanwhile, there has been no findings regarding the relationship between a stressed state and the eye tissue including the choroid.

A method for detecting a stressed state according to the present embodiment is, preferably, a method in which a stressed state of the subject is detected based on a tomographic image of the choroid of the subject. From a tomographic image of the choroid, it is possible to discern the state of the choroid in detail, including the morphology of the choroid such as the choroidal thickness and the volume of the choroid.

The tomographic image of the choroid is a tomographic image of the eye including the choroid, and is preferably a tomographic image of the fundus including the choroid. In order to calculate feature values of the choroid such as the thickness and volume of the choroid, it is preferable that the boundary between the choroid and the retina and the boundary between the choroid and the sclera can be extracted. Therefore, it is preferable that the tomographic image of the choroid includes, at least, a part of the retina and a part of the sclera in addition to the choroid. The tomographic image of the choroid may be, for example, a tomographic image of a region including a position below the fovea of the retina, or a region including a position away from the fovea by a predetermined distance in a predetermined direction with respect to the fovea of the retina. Alternatively, the tomographic image of the choroid may be a tomographic image of a region including the optic disc, or a region including a position away from the optic disc by a predetermined distance in a predetermined direction with reference to the optic disc. Furthermore, the tomographic image of the choroid may be a tomographic image including a plurality of regions. From the viewpoint of ease of acquiring a tomographic image, it is particularly preferable that the tomographic image of the choroid is a tomographic image of a region including a position below the fovea of the retina. In addition, the tomographic image of the choroid may be a one-dimensional image, a two-dimensional image, or a three-dimensional image.

A tomographic image of the choroid can be acquired by forming a tomographic image of the choroid using a well-known technique in the art. Preferably, a tomographic image of the choroid is formed using an apparatus that is based on optical coherence tomography (hereinafter abbreviated as "OCT") (hereinafter referred to as an "OCT apparatus"). The OCT apparatus is an interference optical apparatus that splits a light beam emitted from a light source, and causes light reflected or scattered from a predetermined position of a subject where measurement light is incident, and reference light reflected from a reference object, to interfere with each other. OCT is a technology that uses interference light to form an image of the structure of a subject in the depth direction at a position where measurement light is incident. With OCT, it is possible to acquire a high-resolution tomographic image of the subject. That is to say, an OCT apparatus can non-invasively acquire a high-resolution tomographic image of the fundus including the choroid by irradiating the fundus with measurement light. In addition, an OCT apparatus is an apparatus that can objectively examine the choroid, and is an apparatus for short-time non-invasive examinations that are routinely performed in ophthalmologic examinations. Therefore, an OCT apparatus does not place a heavy burden on the subject.

A time-domain OCT (hereinafter abbreviated as a "TD-OCT") that causes light wave interference in the time domain, or a Fourier-domain OCT (hereinafter abbreviated as an "FD-OCT") that causes light wave interference in the frequency domain or the wavelength domain may be employed in the OCT apparatus, for example. Preferably, an FD-OCT is employed. Examples of FD-OCTs include a spectral-domain OCT (hereinafter abbreviated as an "SD-OCT") that utilizes a broadband light source, and a swept-source OCT (hereinafter abbreviated as an "SS-OCT") that utilizes a wavelength-swept laser. Preferably, an SS-OCT is employed. Furthermore, an EDI-OCT that utilizes enhanced depth imaging (hereinafter abbreviated as an "EDI") and a high-penetration-OCT (hereinafter abbreviated as an "HP-OCT") that utilizes a long wavelength light source may be employed, for example. It is preferable that a 1 μm band light source that typically emits light with a wavelength of approximately 950 nm to 1100 nm is employed, and it is particularly preferable that a light source that emits light with a wavelength of 1050 nm is employed. When a 1 μm band light source is employed, light is less likely to be affected by absorption in the retinal pigment epithelium or scattering due to turbidity, if present, in the intermediate translucent body, for example. Therefore, it is possible to acquire a clearer image of deep tissue such as the fundus including the choroid.

Specifically, by irradiating the fundus of the subject with measurement light, it is possible to acquire a one-dimensional tomographic image (z image) of the fundus including the choroid at the irradiated position taken in the depth direction (z direction). Furthermore, by performing one-dimensionally scanning on the fundus of the subject with the irradiated position being moved in the direction (x direction) that is orthogonal to the depth direction, it is possible to acquire a two-dimensional tomographic image (xz image) of the fundus including the choroid. One-dimensional scanning can be performed along a predetermined straight line or curved line. Thus, it is possible to acquire a two-dimensional tomographic image taken in the depth direction along the scanning direction of measurement light. Also, by performing two-dimensional scanning on the fundus with the irradiated position being moved in the directions (x and y directions) that are orthogonal to the depth direction, it is possible to acquire a three-dimensional image (xyz image) including the choroid. At this time, two-dimensional scanning can be performed within a predetermined area. That is, it is possible to construct a three-dimensional tomographic image from a plurality of two-dimensional images acquired by repeatedly scanning the fundus of the subject with measurement light, within the predetermined region, while shifting the position of measurement light. Thus, it is possible to capture a three-dimensional structure of the fundus including the choroid. In particular, an SS-OCT can scan a wide range of 3 to 12 mm in the x and y directions in a few seconds and acquire an image in the depth direction, and therefore can construct a clear three-dimensional tomographic image of the fundus including the choroid.

In addition, the time required for an OCT apparatus to acquire a tomographic image of the choroid is approximately 3 seconds, and therefore an OCT apparatus is also advantageous in that the image is less likely to be affected by eye movements.

It is preferable that a tomographic image of the choroid is not acquired during or immediately after exercise. For example, regarding the choroidal thickness, it has been reported that the choroid became significantly thicker for at least five minutes in a case of moderately intense low-load exercise (for example, see Sayin N, et al., Indian J Ophthalmol. 2015, 63(5), 445-450). On the other hand, it has also been reported that there was no significant difference in the choroidal thickness after 15 minutes, compared with the baseline. Therefore, if the subject has performed exercise with a higher intensity than daily activities, it is preferable to acquire a tomographic image of the choroid when a predetermined time (for example, 15 minutes or 30 minutes) has elapsed after the end of the exercise. Further, a tomographic image of the choroid is generally acquired when the subject is in a sitting position, and a tomographic image of the choroid of either one of the left and right eyes, or tomographic images of the choroids of both eyes may be acquired.

The step of detecting a stressed state may include calculating a choroidal thickness based on the tomographic image, and detecting a stressed state of the subject based on the calculated choroidal thickness. The choroidal thickness is the thickness of the choroid, and can be calculated from the tomographic image of the choroid as, for example, the vertical distance from the boundary line between the retinal pigment epithelium located on the outermost side of the retina and the choroid to the boundary line between the choroid and the sclera. The position of the boundary between the retinal pigment epithelium and the choroid, and the position of the boundary between the choroid and the sclera, can be specified using a well-known image processing technique in the art. For example, the positions of these boundaries can be specified from changes in pixel values (for example, brightness values) in tomographic images. Also, the choroidal thickness may be calculated using the arithmetic function of a computer, for example.

The choroidal thickness is preferably calculated at a predetermined position of the choroid. For example, the choroidal thickness may be calculated at the position of the fovea of the retina, or a position away from the fovea by a predetermined distance in a predetermined direction (for example, in an upward or downward direction or a direction toward the nose or the ear) with reference to the fovea of the retina. Alternatively, the choroidal thickness may be calculated at the position of the optic disc or at a position away from the optic disc in a predetermined direction by a predetermined distance with reference to the optic disc. Furthermore, the choroidal thickness may be measured at a plurality of positions. A particularly preferred choroidal thickness is that measured at a position below the fovea of the retina. The choroidal thickness may be calculated for the choroid of either one of the left and right eyes, or for the choroids of both eyes. Also, after the choroidal thickness has been calculated for both eyes, only a thinner choroid or a thicker choroid may be used for the detection of a stressed state. Preferably, a thicker choroid, which exhibits a higher degree of correlation with a stressed state, is used for detection.

In a subject in a stressed state, the choroidal thickness is significantly larger than that of a healthy and unstressed normal control group. For example, it is envisaged that the choroidal blood vessels of a high-stress person are expanded and the choroid is thick due to overstimulated autonomic nerves. Specifically, a subject in a stressed state can be detected by comparing the choroidal thickness calculated from a tomographic image of the choroid of the subject with, for example, a reference value calculated in advance from tomographic images of the choroids of healthy bodies that are not in a stressed state. If the value of the choroidal thickness of the subject is higher than the reference value, the subject is detected as being in a stressed state, and if the value is lower than the reference value, the subject is detected as not being in a stressed state. Note that healthy bodies that are not in a stressed state and are used to calculate the reference value can be selected using a stress detection method that involves other well-known stress markers, such as the brief job stress questionnaire (57 items) or the Japanese version of the mood/anxiety disorder questionnaire (K6) recommended by the Ministry of Health, Labor and Welfare of Japan, and preferably a plurality of stress detection methods are performed. The reference value is preferably calculated as the average value of a plurality of healthy bodies. Once the reference value is determined, a stressed state can be detected using the reference value. In the case of an adult, for example, the reference value may be set to 250 μm, 300 μm, or any value lower than that, at a position below the fovea, and is preferably set to any value in the range of 200 to 300 μm at a position below the fovea.

The step of detecting a stressed state may include a step of correcting the calculated choroidal thickness of the subject based on at least one factor selected from among a detection time, the subject's age, sex, and history of present illness, and an indicator obtained from an eye structure, such as an eye axial length or an equivalent spherical area. For example, it has been reported that the choroidal thickness has a negative correlation with age, and the choroid becomes thin with age (Wakatsuki Y et al., PLoS One. 2015 Dec. 3; 10 (12): e0144156). It has been reported that the choroidal thickness exhibits diurnal fluctuations, and the choroid is thick in the early morning, but gradually becomes thinner during the daytime, and that there is no difference in the fluctuation range of the choroidal thickness between the left and right eyes, for example (for example, see Tan C S et al., Invest Ophthalmol Vis Sci, 2012; 53(1): 261-266, etc.). Furthermore, it has been reported that some eye diseases and systemic diseased conditions affect the choroidal thickness, and, for example, the choroid thickness significantly increases under central serous chorioretinopathy and Harada disease, whereas the choroid thickness decreases under high myopia, age-related macular degeneration, glaucoma, diabetic retinopathy, and the like. Furthermore, it has also been reported regarding a relationship with the eye axis and the equivalent spherical area in addition to age (for example, see Tan C S et al., Invest Ophthalmol Vis Sci, 2012; 53(1): 261-266, Ikuno Y et al., Invest Ophthalmol Vis Sci, 2010; 51(4): 2173-2176, Wen Bin Wei et al., Ophthalmology, 2013; 120(1): 175-180), etc.), and it has been reported that the shorter the eye axial length is, or the larger the equivalent sphere area is, the thicker the choroid is, for example. Furthermore, it has been reported that the flatter the cornea is, or the better the corrected vision is, the thicker the choroid is. On the other hand, it has also been reported that the choroidal thickness is not particular correlated with blood pressure, ocular perfusion pressure, intraocular pressure, smoking, alcohol consumption, blood lipid/glucose concentration, diabetes, or arterial hypertension, for example (see the aforementioned Wen Bin Wei et al., Ophthalmology, 2013; 120(1): 175-180, etc.). Therefore, by correcting the influence of the above factors on the choroidal thickness, it is possible to more accurately detect a stressed state of the subject.

For example, when the choroidal thickness varies due to numerical fluctuations of the above factors such as the detection time and age, the choroidal thickness calculated from a group of which the above factors have standard values and that is not in a stressed state is determined as a standard choroidal thickness. Then, the ratio of the standard choroidal thickness to the choroidal thickness calculated from the group of which the above factors do not have standard values and that is not in a stressed state (the standard choroidal thickness divided by the calculated choroidal thickness) is used as a correction coefficient. By multiplying the calculated choroidal thickness by the correction coefficient, it is possible to correct the choroidal thickness calculated from the subject of which the corresponding factors do not have standard values. Further, if a correlation between the numerical fluctuations of the above factors and the fluctuation of the choroidal thickness can be obtained, the choroidal thickness can be corrected based on such a correlation. For example, if the factor is sex, the choroidal thickness corresponding to one sex can be corrected based on the choroidal thickness corresponding to the other sex. Further, for example, if the choroidal thickness varies depending on the presence or absence of a factor such as the history of present illness, the choroidal thickness calculated from a group that does not have any of the above factors and is not in a stressed state is determined as the standard choroidal thickness, the ratio of the standard choroidal thickness to the choroidal thickness calculated from the group that has any one of the above factors and is not in a stressed state (the standard choroidal thickness divided by the calculated choroidal thickness) is determined as the correction coefficient, and the choroidal thickness calculated from the subject that has the corresponding factor can be corrected based on such a correction coefficient. As with the calculation of the choroidal thickness, the correction may be performed using the arithmetic function of a computer, for example.

The step of detecting a stressed state may include calculating the volume of the choroid from the tomographic image, and detecting a stressed state of the subject based on the calculated volume of the choroid. The volume of the choroid may be the volume of the portion surrounded by the boundary line between the retinal pigment epithelium located at the outermost side of the retina and the choroid, and the boundary line between the choroid and the sclera, and can be calculated based on the above-described choroid thickness. The volume of the choroid may be calculated using the arithmetic function of a computer, for example.

The volume of the choroid is preferably calculated for a predetermined region of the choroid. For example, the volume of the choroid may be calculated for a region centered around the position of the fovea of the retina, or a position away from the fovea by a predetermined distance in a predetermined direction (in a direction (x direction) that is orthogonal to the depth direction (z direction), e.g. in an upward or downward direction or a direction toward the nose or the ear) with reference to the fovea of the retina. Alternatively, the volume of the choroid may be calculated for a region centered around the position of the optic disc, or a position away from the optic disc in a predetermined direction by a predetermined distance with reference to the optic disc. Furthermore, the volume of the choroid may be calculated for a plurality of regions. A particularly preferred volume of the choroid is that for a region centered around a position below the fovea of the retina. The dimensions of the region for which the volume of the choroid is calculated is not particularly limited, but may be 3 mm×3 mm, 6 mm×6 mm, or 10 mm×10 mm, for example. The volume of the choroid may be calculated for the choroid of either one of the left and right eyes, or for the choroids of both eyes. Also, after the choroidal thickness has been calculated for both eyes, only the choroid with a larger volume, or the choroid with a smaller volume may be used for the detection of a stressed state.

In a subject in a stressed state, the volume of the choroid is significantly larger than that of a healthy and unstressed normal control group. A stressed state of the subject can be detected by comparing the volume of the choroid calculated from a tomographic image of the choroid of the subject with, for example, a reference value calculated in advance from tomographic images of the choroids of healthy bodies that are not in a stressed state. If the value of the volume of the choroid of the subject is higher than the reference value, the subject is detected as being in a stressed state, and if the value is lower than the reference value, the subject is detected as not being in a stressed state.

In the case of an adult, for example, the reference value may be set to any value no greater than 24.3 mm3, preferably 20.3 mm3 in a region of 9 mm×9 mm (12 mm×9 mm at maximum) centered around the fovea.

Furthermore, the method for detecting a stressed state according to the present embodiment may be configured to measure the intensity of the stress on the subject based on the volume of the choroid calculated from a tomographic image of the choroid of the subject.

The step of detecting a stressed state may include a step of correcting the calculated volume of the choroid based on at least one factor selected from among a detection time, the subject's age, sex, and history of present illness, and an indicator obtained from an eye structure. Here, the indicator obtained from an eye structure may be an eye axial length or an equivalent spherical area, for example, but are not limited to them. The volume of the choroid is also affected by the above factors as with the above-described choroidal thickness. Therefore, by correcting the influence of the above factors on the volume of the choroid, it is possible to more accurately detect a stressed state of the subject.

For example, when the volume of the choroid varies due to numerical fluctuations of the above factors such as the detection time and age, the volume of the choroid calculated from a group of which the above factors have standard values and that is not in a stressed state is determined as a standard volume. Then, the ratio of the standard volume to the volume of the choroid calculated from the group of which the above factors do not have standard values and that is not in a stressed state (the standard volume divided by the calculated volume of the choroid) is used as a correction coefficient. By multiplying the calculated volume of the choroid by the correction coefficient, it is possible to correct the volume of the choroid calculated from the subject of which the corresponding factors do not have standard values. If a correlation between the numerical fluctuations of the above factors and the fluctuation of the volume of the choroid can be obtained, the volume of the choroid can be corrected based on such a correlation. For example, if the factor is sex, the volume of the choroid corresponding to one sex can be corrected based on the volume of the choroid corresponding to the other sex. Also, for example, if the volume of the choroid varies depending on the presence or absence of a factor such as the history of present illness, the volume of the choroid calculated from a group that does not have any of the above factors and is not in a stressed state is determined as the standard volume, the ratio of the standard volume to the volume of the choroid calculated from the group that has any one of the above factors and is not in a stressed state (the standard volume divided by the calculated volume of the choroid) is determined as the correction coefficient, and the volume of the choroid calculated from the subject that has the corresponding factor can be corrected based on such a correction coefficient. As with the calculation of the volume of the choroid or the like, the correction may be performed using the arithmetic function of a computer, for example.

With the method for detecting a stressed state according to the present embodiment, it is possible to objectively detect a stressed state of the subject. Also, since the choroid precisely reflects a stressed state of a living body, it is possible to accurately detect a stressed state of the subject. Therefore, there is no room for misdetection or the like of a stressed state caused by the subject intentionally changing their answers, which is a problem in conventional subjective stress detection methods such as the stress check, and a high stress person can be reliably selected.

Furthermore, by using the optical coherence tomography, it is possible to non-invasively and easily detect a stressed state without contact in a short time. Therefore, it is possible to reduce mental and physical burdens on the subject. Therefore, the stress load at the time of detection can be eliminated, and a stressed state of the subject can be accurately detected. Furthermore, there is an advantage in that the influence of the eye movement is small. In addition, conventional biomarkers are problematic in that a stressed state cannot be easily discerned because they decompose and disappear in a short time even if they appear in a living body in response to stress. However, with the method for detecting a stressed state according to the present embodiment, such a problem does not occur. Also, the method for detecting a stressed state according to the present embodiment may be configured to automatically detect a stressed state by employing an assessment means using a stress detection apparatus described below, a computer, or the like.

Therefore, with the method for detecting a stressed state according to the present embodiment, it is possible to reliably detect a subject in a stressed state. It is possible to recommend a subject detected as being in a stressed state to consult with or take counseling at an appropriate medical institution. In particular, with the method for detecting a stressed state according to the present embodiment, it is possible to detect even a latent stressed state in which stress has not become apparent as a specific symptom, disease, or the like. Therefore, it is possible to detect a stressed state at an early stage, which leads to the prevention of symptoms and diseases caused by stress. Therefore, the method for detecting a stressed state according to the present embodiment can be desirably used for periodical health checkups for workers and the like, which contribute to physical and mental health management of workers, for example. As a result, the method leads to improvement of the working environment, increases work efficiency, and contributes to improvement of labor productivity.

Stress Detection Apparatus

As shown in FIG. 1, a stress detection apparatus X according to the present embodiment may include, for example, an image acquisition unit 11, an input unit 12, a computation unit 13, a detection unit 14, a storage unit 15, a display unit 16, and so on. The stress detection apparatus X according to the present embodiment is constituted by a desktop personal computer, a laptop personal computer, a tablet terminal, or the like, and can communicate with an OCT apparatus 10 wirelessly or by wire, using the image acquisition unit 11 as a communication interface. The computation unit 13 and the detection unit 14 are configured by hardware or software or both, using a CPU as a core member, the storage unit 15 is constituted by a ROM, a RAM, and so on, and the display unit 16 is constituted by a well-known display such as a liquid crystal screen. Note that the stress detection apparatus X may be provided integrally with the OCT apparatus 10, or one or more functions of the functions of the computation unit 13, for example, may be built into the OCT apparatus 10. There is no particular limitation.

The image acquisition unit 11 acquires tomographic image information regarding the fundus including the choroid, of the subject from the OCT apparatus 10 described above. The OCT apparatus 10 may include: a light source; a measurement optical system that splits a light beam emitted from the light source, to irradiate the inside of the eye to be examined, and guides the measurement light from the fundus of the subject; a reference optical system that splits a light beam emitted from the light source, to irradiate a reference object, and guides reference light that is light reflected from the reference object; and a light receiving element that receives interference light that is a combination of the measurement light guided by the measurement optical system and the reference light guided by the reference optical system, converts the interference light into an electric signal, and outputs the electric signal.

The input unit 12 accepts an operation input by an operator, and outputs an operation input signal corresponding to the operation input, to the computation unit 13. The input unit 12 is constituted by a button, a switch, a keyboard, and so on. The input unit 12 can be used to input information regarding the subject (age, sex, the history of present illness, the eye axial length, and so on) and a detection date, for example.

The computation unit 13 processes a tomographic image signal acquired by the image acquisition unit 11. The computation unit 13 includes an image signal processing unit 13*a* and a calculation unit 13*b*, for example.

The image signal processing unit 13*a* generates a tomographic image of the fundus including the choroid by performing various kinds of image processing and the like based on the output signal from the image acquisition unit 11. The tomographic image generated by the image signal processing unit 13*a* is stored in the storage unit 15, and is also output to the display unit 16.

The calculation unit 13*b* calculates a feature value of the choroid, based on the tomographic image of the fundus including the choroid, generated by the image signal processing unit 13*a*. Examples of feature values of the choroid include the choroidal thickness and the volume of the choroid of the subject, and so on. The definitions of the choroidal thickness and the volume of the choroid are as described in the above "Method for Detecting Stressed State" section.

The choroidal thickness can be calculated by specifying the boundary line between the retinal pigment epithelium and the choroid and the boundary line between the choroid and the sclera, and measuring the vertical distance between these boundary lines. The boundary line between the retinal pigment epithelium and the choroid, and the boundary line between the choroid and the sclera can be specified by applying a well-known image processing technique, or automatically specified according to a preset algorithm.

For example, it is possible to extract the boundary lines by searching for pixel values (for example, brightness values) in the depth direction in a tomographic image of the choroid, and detecting changes in the pixel values. If it is difficult to automatically extract the boundary lines because of small changes in the pixel values, the operator may visually check the tomographic image displayed on the display unit and specify the boundary lines by manually writing the boundaries in the tomographic image, for example.

The choroidal thickness is measured by measuring the distance between the boundary lines specified above, at a predetermined measurement position. The distance may be measured by, for example, counting the number of pixels arranged in the depth direction between these boundaries in the tomographic image.

The position of the fovea of the retina or the optic disc, which serves as a reference for the calculation of the choroidal value, can be automatically specified in a tomographic image of the choroid by applying a well-known image processing technique. Alternatively, such a position may be manually specified by the operator.

The volume of the choroid can be calculated by adding information regarding the thickness calculated above to the three-dimensional tomographic image of the choroid, and preferably a volume within a preset specific region is calculated.

The calculation unit 13*b* can correct the feature value of the choroid calculated by the calculation unit 13*b* based on the tomographic image of the choroid, in order to eliminate the influence of factors that affect the feature value of the choroid, such as a detection time, the subject's age, sex, and history of present illness, and an indicator obtained from an eye structure, such as the eye axial length or the equivalent spherical area, input using the input unit 12, for example.

The correction of the feature value of the choroid is the same as the above-described correction, and thus a description thereof is omitted.

The detection unit 14 detects a stressed state of the subject based on the feature value of the choroid, calculated by the calculation unit 13b based on the tomographic image of the choroid. The detection unit 14 performs detection to determine whether or not the feature value of the choroid calculated by the calculation unit 13b is no less than the reference value calculated in advance from tomographic images of the choroids of healthy bodies that are not in a stressed state, stored in the storage unit 15. Such a comparison between the feature value of the choroid of the subject and the reference value can be performed based on a well-known statistical method. The detection unit 14 stores the result of detection in the storage unit 15 and outputs them to the display unit 16, as the result of detection of a stressed state.

The storage unit 15 stores input data such as information regarding the subject, the inspection date, and so on input by the operator from the input unit 12, a tomographic image of the choroid formed by the image signal processing unit 13a of the computation unit 13, the feature value of the choroid of the subject calculated by the calculation unit 13b, and information such as a stressed state detected by the detection unit 14. The storage unit 15 also stores a calculation program for calculating the feature value of the choroid, a detection program for detecting a stressed state, a reference value used for the detection, and so on. Furthermore, the storage unit 15 stores, for example, a correction program for correcting the effects of factors that are known to affect the feature value of the choroid, such as a detection time, the subject's age, sex, and history of present illness, and an indicator obtained from an eye structure, such as the eye axial length or the equivalent spherical area.

The display unit 16 displays, for example, information regarding the subject, the inspection date, and so on input from the input unit, a tomographic image of the choroid formed by the image signal processing unit, the feature value of the choroid calculated by the calculation unit from a tomographic image of the choroid, and the result of detection of a stressed state, detected based on the feature value of the choroid, by the detection unit performing a comparison with the reference value. In addition, the display unit 16 can display a warning indicating that consultation or counseling is necessary, if stressed state is detected as a result of detection.

An example of an operation of the stress detection apparatus X according to the present embodiment will be described with reference to the flowchart shown in FIG. 2.

Step S101

A tomographic image signal (tomographic image data) regarding the eye of the subject captured by the OCT apparatus 10 is acquired by the image acquisition unit 11.

Step S102

Next, based on the tomographic image signal acquired by the image signal processing unit 13a, the image signal processing unit 13a performs various kinds of image processing and the like to generate a tomographic image of the fundus including the choroid. At this time, the tomographic image of the fundus including the choroid generated by the image signal processing unit 13a may be stored in the storage unit 15, and the tomographic image of the fundus including the choroid may be displayed on the display unit 16. It is also possible to employ a configuration in which, if the tomographic image of the choroid deviates from the normal range of the tomographic image of the choroid stored in the storage unit, the operation of the OCT apparatus 10 and the position of the eye of the subject, for example, are appropriately corrected and step S101 is carried out again.

Step S103

The calculation unit 13b calculates the feature value of the choroid (the thickness or volume of the choroid) according to a calculation program related to calculation of the feature value of the choroid stored in the storage unit 15, based on the tomographic image of the fundus including the choroid generated by the image signal processing unit 13a, and performs control to output information regarding the calculated feature value of the choroid to the display unit 16. At this time, the calculation unit 13b may correct the feature value of the choroid as necessary according to a correction program related to correction of the feature value of the choroid stored in the storage unit 15. Also, the display unit 16 may display an image showing the feature value of the choroid and the content of correction based on input information.

Step S104

The detection unit 14 detects whether or not the subject is in a stressed state, based on information regarding the feature value of the choroid calculated by the calculation unit 13b and the reference value for the feature value of the choroid stored in the storage unit 15. Specifically, the detection unit 14 detects that the subject is in a stressed state if the feature value of the choroid is no less than the reference value, and detects that the subject is not in a stressed state if the feature value of the choroid is less than the reference value.

Next, the result of detection by the detection unit 14 is output to the display unit 16, and the display unit 16 displays the state of stress of the subject based on the information input thereto. At this point, it is possible to employ a configuration in which a warning indicating that consultation or counseling is necessary is displayed if a stressed state is detected as a result of detection by the detection unit 14. Note that the detection unit 14 may detect a stressed state on a multiple-level scale, and the display unit 16 may display characters such as "high stress", "middle stress", "low stress", or the like, or display a numerical value indicating one of the multiple levels.

EXAMPLES

The following specifically describes the present invention using examples. However, the present invention is not limited to these examples.

Example 1

Examination of Relationship Between Choroidal Thickness and Stress or Anxiety

In this example, the relationship between stress or anxiety and the thickness of the choroid, which is a part of the eye tissue, was examined. In this case, a relationship with the results of detection performed using a subjective stress detection method was examined.

1. Method 1-1. Examination Period 1-1-1. Examination Date
   3 or 4 consecutive days during a period from July to October, 2017, 1-1-2. Examination Time
   from evening to night
1-2. Subjects Fourteen adults (six males and eight females) randomly selected from the staff of Osaka University Hospital. The profiles of the subjects are summarized in Table 1 below.

TABLE 1

| ID No. | Sex | Age | Occupation | Systemic Disease | Eye Disease | Use of Contact Lenses |
|---|---|---|---|---|---|---|
| DR1 | Female | 35 | Doctor | N/A | Esotropia Dissociated, Vertical Deviation after Surgery | No |
| DR2 | Male | 43 | Doctor | N/A | N/A | No |
| DR3 | Male | 30 | Doctor | N/A | N/A | No |
| DR4 | Male | 30 | Doctor | N/A | Intermittent Exotropia | No |
| DR5 | Male | 36 | Doctor | Arrhythmia | N/A | No |
| ORT1 | Female | 27 | Orthoptist | N/A | N/A | No |
| ORT2 | Female | 22 | Orthoptist | N/A | N/A | No |
| ORT3 | Female | 22 | Orthoptist | N/A | N/A | No |
| ORT5 | Female | 28 | Orthoptist | N/A | N/A | No |
| ORT6 | Female | 25 | Orthoptist | N/A | N/A | Yes |
| ORT7 | Female | 26 | Orthoptist | N/A | N/A | Yes |
| DR6 | Male | 48 | Doctor | N/A | N/A | Yes |
| DR7 | Male | 41 | Doctor | N/A | N/A | No |
| ORT9 | Female | 25 | Orthoptist | N/A | N/A | No |

1-3. Examination Method

A stressed state of the subject were examined using the following three kinds of methods.

1-3-1. Examination Based on Choroidal Thickness

The choroidal thickness of each subject was measured using an SS-OCT (TOPCON (registered trademark) SS-OCT manufactured by TOPON). The choroid was measured by measuring the fovea choroidal thickness. Specifically, a tomographic image of the fundus was acquired so that the fovea retina was as orthogonal as possible to the tomographic surface, and a vertical ruled line was drawn from a position immediately below the retinal pigment epithelium of the fovea to a position that appears to be the lower edge of the choroid, and the length of the line was measured as the fovea choroidal thickness. When a tomographic image was to be acquired, the position of the fixation point was finely adjusted so that the fovea was located at the center of the tomographic image. Also, the eye axial length of each subject was measured using IOLmaster (manufactured by ZEISS), the blood pressure and the pulse were measured, and a BUT test was performed. In addition, the subjects scored subjective stress felt by themselves through a self-assessment at the time of measurement. Subjective stress was assessed on a five-point scale (5: very often, 4: somewhat often, 3: sometimes, 2: almost never, 1: never).

1-3-2. Examination Based on the Brief Job Stress Questionnaire

The subjects were asked to answer the brief job stress questionnaire (57 items) recommended by the Ministry of Health, Labor and Welfare of Japan (see "http://www.mhlw.go.jp/bunya/roudoukijun/anzeneisei12/dl/stress-check_j.pdf), and the answers to the questionnaire were scored using a raw score conversion table. The brief job stress questionnaire (57 items) is divided into three areas, namely A area (factors that are considered to be causes of stress), B area (psychosomatic reactions caused by stress), and C area (other factors that affect stress reactions). High-stress people were selected using the raw score conversion table, based on the implementation manual for the Stress Check System based on the Industrial Safety and Health Act" (see "http://www.mhlw.go.jp/bunya/roudoukijun/anzeneisei12/pdf/150803-1.pdf").

1-3-3. Examination Based on Japanese Version of the Mood/Anxiety Disorder Questionnaire (K6)

The subjects were asked to answer the Japanese version of the mood/anxiety disorder questionnaire (K6) (see "http://www.city.noshiro.akita.jp/upload/download/118779download.pdf"), and the answers to the questionnaire were collected. K6 is a 6-item, 5-point scale for measuring mood/anxiety disorders, developed by Kessler and so on (see Kessler R C et al., Psychological Medicine, 2002, 32, 959-976, etc.), and it has been reported that this scale is applicable in Japan as well (see Sakurai K et al., Psychiatry Clin Neurosci., 2011; 65(5): 434-441, etc.). The cut-off value was determined based on reports such as the aforementioned Sakurai K et al., Psychiatry Clin Neurosci., 2011; 65(5): 434-441, Kessler R C et al., ARCH GEN PSYCHIATRY 2003; 60: 184-189, Bert L R Cornelius et al., BMC Public Health, 2013; 13: 128, Hirohito NANBU, et al, Kousei No Shihyo, May 2014, Volume 61, Issue 5, pages 23-30, and Norito KAWAKAMI, et al., Health and Labor Sciences Research Grant for 2014 (a project for Research on Psychiatric and Neurological Diseases and Mental Health) "Research on suicide prevention based on trends", allotted research report "Study of mental health for prevention of suicide among adults", etc.

2. Results 2-1. Measured Items

Table 2 shown below summarizes the results of measurement of the average fovea choroidal thickness, axial length, blood pressure, pulse, and BUT test of each subject.

TABLE 2

| ID No. | Blood Pressure (mmHg) | Pulse (/min) | Eye Axial Length (mm) | | Average Fovea Choroidal Thickness (μm) | | BUT (sec) | | Brake Pattern |
|---|---|---|---|---|---|---|---|---|---|
| | | | Right | Left | Right | Left | Right | Left | |
| DR1 | 108/66 | 66 | 24.1 | 23.4 | 410 ± 27 | 467 ± 28 | >5 | >5 | |
| DR2 | 103/61 | 67 | 25.6 | 25.7 | 197 ± 10 | 237 ± 15 | 4-5 | 2 | Dimple break Random break |
| DR3 | 109/58 | 68 | 27.4 | 27.4 | 270 ± 9 | 264 ± 9 | 4 | >5 | Spot break |
| DR4 | 118/74 | 68 | 24.2 | 24.2 | 370 ± 10 | 382 ± 6 | 1 | 1-2 | Dimple break |
| DR5 | 108/69 | | 25.3 | 25.5 | 266 ± 6 | 312 ± 10 | Not Measured | Not Measured | |
| ORT1 | 112/75 | 65 | 25.1 | 24.7 | 351 ± 3 | 355 ± 6 | >5 | 4 | Line break |
| ORT2 | 110/75 | 70 | 23 | 23.1 | 512 ± 21 | 462 ± 12 | >5 | >5 | |
| ORT3 | 101/60 | 96 | 23.5 | 23.5 | 332 ± 9 | 413 ± 22 | >5 | 3 | |
| ORT5 | 93/41 | 63 | 24.5 | 24.4 | 266 ± 6 | 334 ± 18 | 4 | 2 | Spot break |
| ORT6 | 105/69 | 78 | 24.4 | 24.2 | 249 ± 18 | 288 ± 12 | 5 | 4-5 | |
| ORT7 | 97/60 | 65 | 25 | 25.1 | 262 ± 3 | 276 ± 9 | >5 | >5 | |
| DR6 | 117/83 | 63 | 26.5 | 25.8 | 209 ± 15 | 261 ± 10 | Not Measured | Not Measured | |
| DR7 | Not Measured | Not Measured | 25.2 | 23.8 | 241 ± 11 | 489 ± 41 | Not Measured | Not Measured | |
| ORT9 | 105/60 | 73 | 22.8 | 23 | 433 ± 17.8 | 316 ± 8.62 | 0 | 0 | Spot break |

2-2. Relationship Between Choroidal Thickness and Subjective Stress

The relationship between the choroidal thickness measured in 1-3-1. above and subjective stress was examined. The results are shown in FIGS. 3 to 5. From the results, it was found that there was a certain tendency that the choroid became thick when the subjective stress was high, and the choroid became thin when the subjective stress was low. However, subjects that had a large choroidal thickness despite a low subjective stress were also found. The subjective stress mentioned here is stress reported by the subjects themselves through a questionnaire, and therefore the subjects can change answers even if they feel stress. In contrast, the measurement of the choroid is an objective test and may directly reflect the physical findings of the subjects, and may reflect true stress.

2-3. Relationship Between Choroidal Thickness and Results of Brief Job Stress Questionnaire (57 Items)

Figure 8:
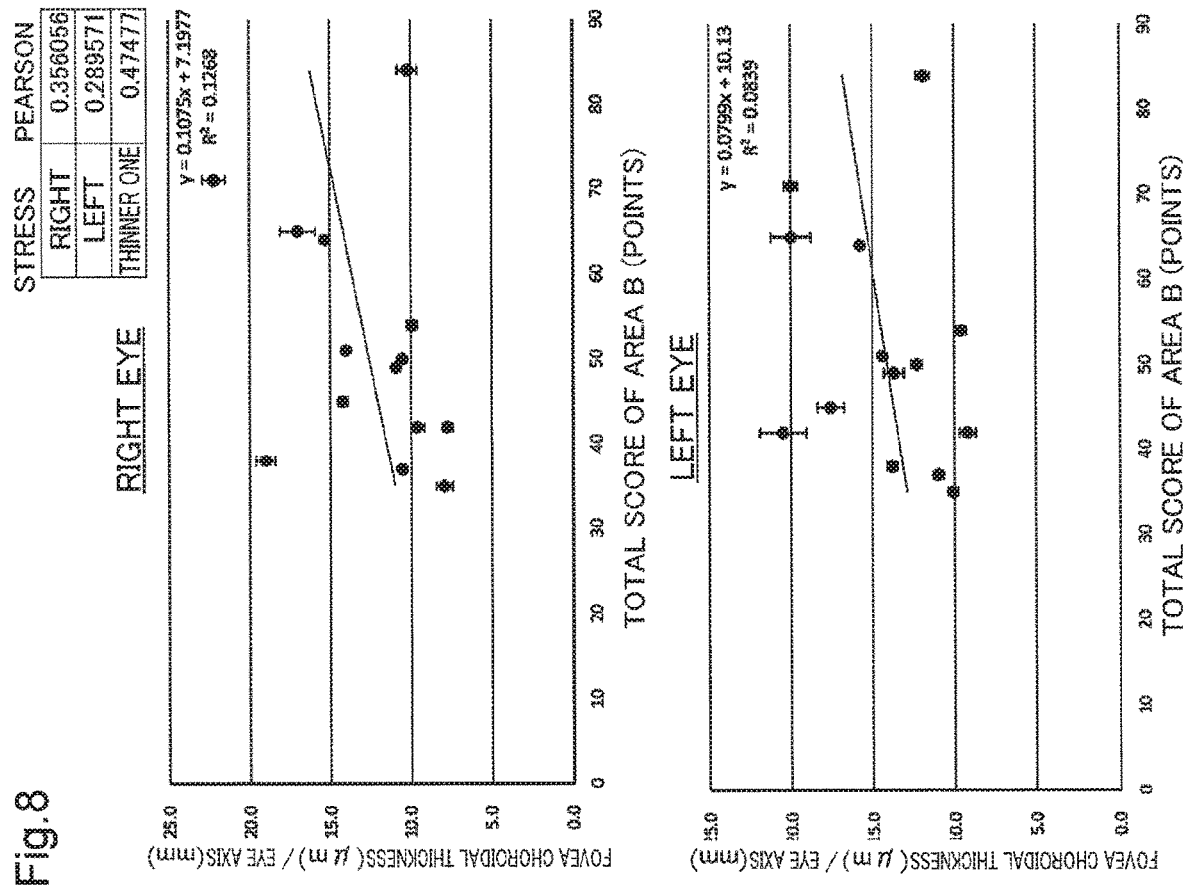
FIG. 8 shows results of Example 1 in which the relationship between the choroidal thickness and stress or anxiety was examined, and is a graph showing results of examination of a relationship between the choroidal thickness divided by the eye axial length and psychosomatic reactions (B area) caused by the stress indicated by the brief job stress questionnaire (57 items).

The relationship between the choroidal thickness measured in 1-3-1. above and the results of the brief job stress questionnaire (57 items) used in 1-3-2. above was examined. FIG. 6 shows the results of the brief job stress questionnaire (57 items). FIG. 7 shows the results of examination of the relationship between the choroidal thickness and the psychosomatic reactions (B area) caused by the stress indicated by the brief job stress questionnaire (57 items), and FIG. 8 shows the results of examination of the relationship between the choroidal thickness divided by the eye axial length and the psychosomatic reactions (B area) caused by the stress indicated by the brief job stress questionnaire (57 items). Note that the choroidal thickness is the average fovea choroidal thickness for 3 or 4 days. From the results, a positive correlation was found between the psychosomatic reactions (B area) caused by the stress indicated by the brief job stress questionnaire (57 items) and the choroidal thickness, and it can be understood that the choroid is thick if the psychosomatic responses caused by stress are high, and the choroid is thin if the psychosomatic reactions are low. In particular, a significant correlation was found in the comparison in the case of the thinner choroid (Pearson's correlation coefficient=0.490879 (FIG. 7)). These results revealed that the choroid served as a stress marker. Since the questionnaire of the brief job stress questionnaire (57 items) are converted into scores by applying the answers to calculation values, this questionnaire is considered as a more accurate stress questionnaire. Therefore, it can be understood that data obtained in this section strongly indicates that the choroidal thickness changes in relation to stress.

2-4. Relationship Between Choroidal Thickness and Results of Japanese Version of the Mood/Anxiety Disorder Questionnaire (K6)

The relationship between the choroidal thickness measured in 1-3-1. above and the results of the Japanese version of the mood/anxiety disorder questionnaire (K6) used in 1-3-3. above was examined. FIG. 9 shows the results of the Japanese version of the mood/anxiety disorder questionnaire (K6), and correlation with the psychosomatic reactions (B area) caused by the stress indicated by the brief job stress questionnaire (57 items). From the results, a correlation was found between them.

Figure 10:
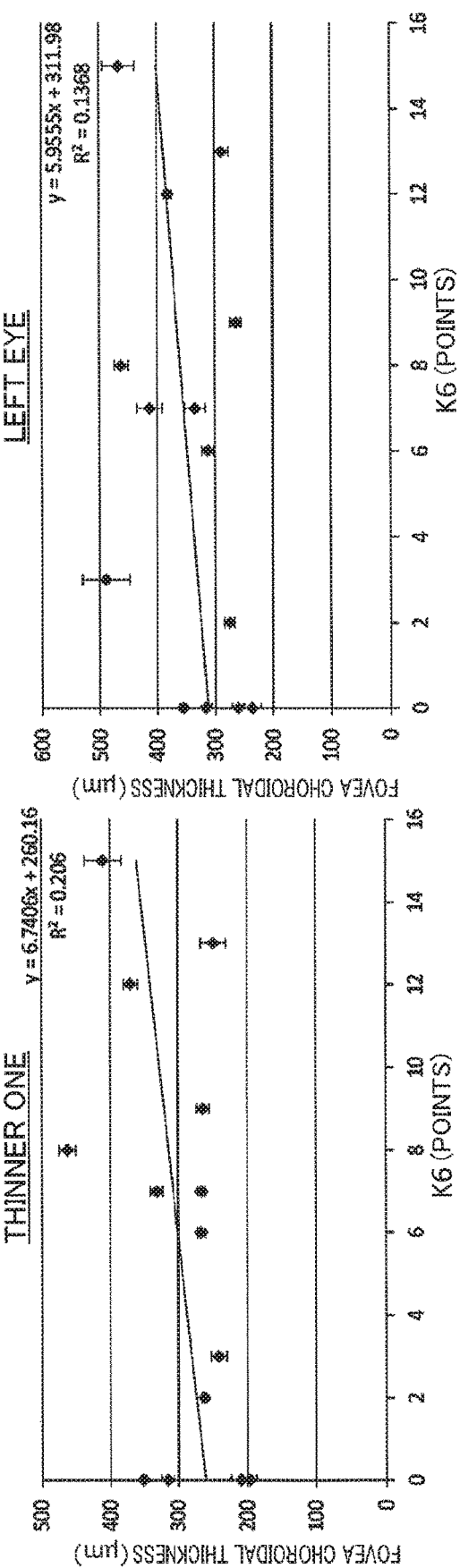
FIG. 10 shows results of Example 1 in which the relationship between the choroidal thickness and stress or anxiety was examined, and is a graph showing results of examination of the relationship between the choroidal thickness and the results of the Japanese version of the mood/anxiety disorder questionnaire (K6).
Figure 11:
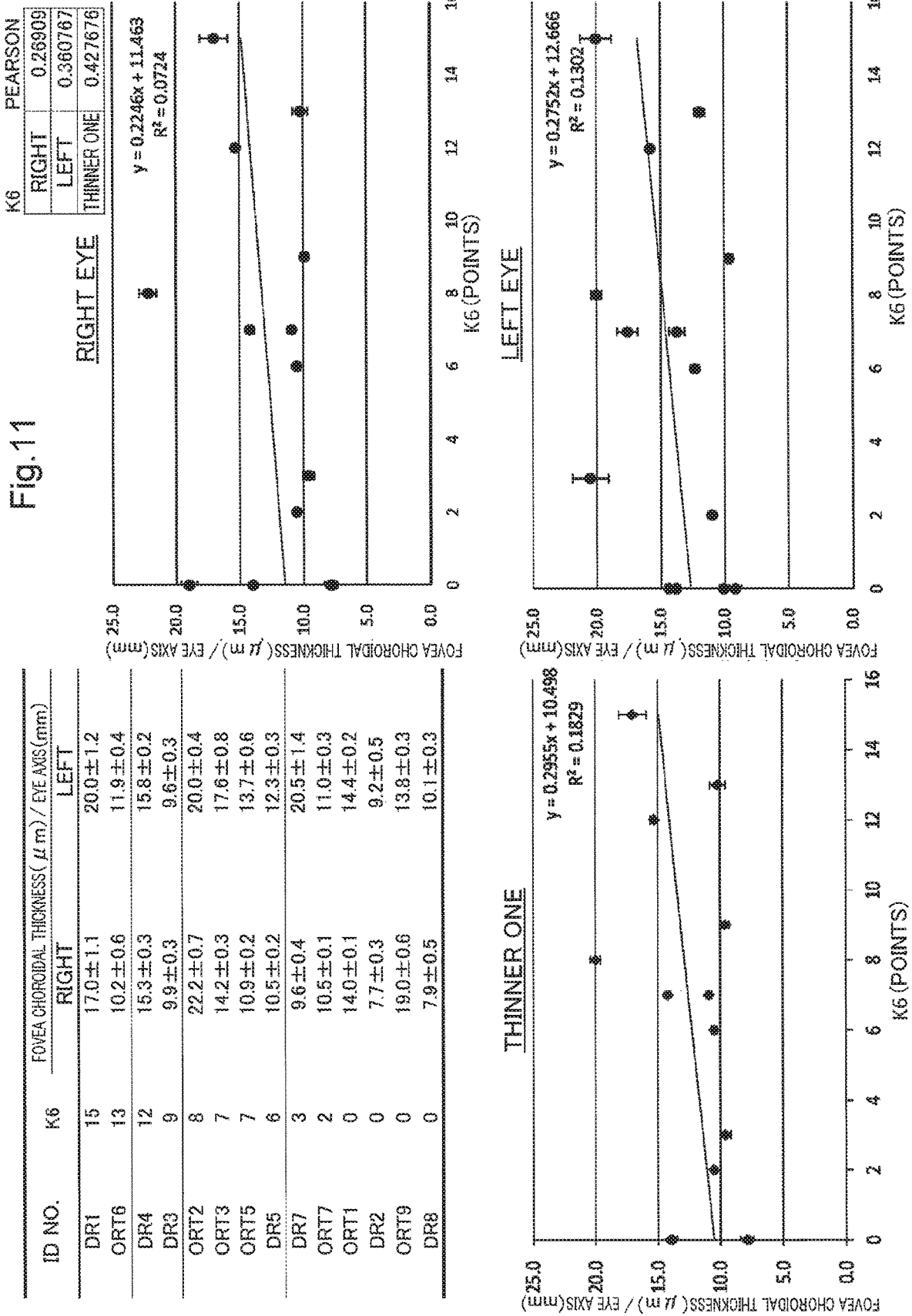
FIG. 11 shows results of Example 1 in which the relationship between the choroidal thickness and stress or anxiety was examined, and is a graph showing results of examination of the relationship between the choroidal thickness divided by the eye axial length and the results of the Japanese version of the mood/anxiety disorder questionnaire (K6).

FIG. 10 shows the results of examination of the relationship between the choroidal thickness and the results of the Japanese version of the mood/anxiety disorder questionnaire (K6), and FIG. 11 shows the results of examination of the relationship between the choroidal thickness divided by the eye axial length and the results of the Japanese version of the mood/anxiety disorder questionnaire (K6). Note that the choroidal thickness is the average fovea choroidal thickness for 3 or 4 days. From the results, a positive correlation was found between results of the Japanese version of the mood/anxiety disorder questionnaire (K6) and the choroidal thickness, and it can be understood that the choroid is thick if the score of K6 is high, and the choroid is thin if the score of K6 is low. In particular, a significant correlation was found in the comparison in the case of the thinner choroid (Pearson's correlation coefficient=0.453832 (FIG. 10)). These results revealed that the choroid served as a stress marker, as with the results obtained in 2-3. The Japanese version of the mood/anxiety disorder questionnaire (K6) is used worldwide. Therefore, it can be understood from the data of this study that it can be naturally said that the choroidal thickness is a stress marker in the world, and it can be understood that the subject is reliably detected as being in a stressed state if the choroid is thick.

2-5. Results of Other Analyses

Tables 3 to 5 shown below summarize the results of consideration of factors that have been reported to affect the choroidal thickness. Table 3 shows the measurement times of the choroidal thickness and the results of measurement of the fovea choroidal thickness (left and right). Table 4 shows the age and the results of measurement of the average fovea choroidal thickness (left and right), and it can be understood that there is a positive correlation between the age and the choroidal thickness. Table 5 shows the sex and the results of measurement of the average fovea choroidal thickness (left and right), and it was found that females tended to have a thicker choroid than males. Therefore, it can be understood that a stressed state of the subject can be more accurately detected based on the choroidal thickness by correcting the measured choroidal thickness with respect to factors that affect the choroidal thickness such as the age and the sex.

Measurement Times and Fovea Choroidal Thickness

TABLE 3

| | | | Fovea Choroidal Thickness (μm) | | | | |
|---|---|---|---|---|---|---|---|
| ID No. | | | $1^{st}$ Day | $2^{nd}$ Day | $3^{rd}$ Day | $4^{th}$ Day | Average ± SD |
| ORT6 | | Measurement Time | 16:20 | 16:50 | 16:40 | | |
| | | Right | 231 | 249 | 266 | | 249 ± 18 |
| | | Left | 278 | 301 | 284 | | 288 ± 12 |
| ORT2 | | Measurement Time | 14:40 | 13:15 | 16:50 | | |
| | | Right | 510 | 492 | 533 | | 512 ± 21 |
| | | Left | 452 | 475 | 458 | | 462 ± 12 |
| DR1 | $1^{st}$ Time | Measurement Time | 17:40 | 16:30 | 16:30 | 16:00 | |
| | | Right | 429 | 388 | 405 | 376 | 400 ± 23 |
| | | Left | 481 | 469 | 487 | 458 | 474 ± 13 |
| | $2^{nd}$ Time | Measurement Time | 17:30 | 16:30 | 16:10 | 17:10 | |
| | | Right | 405 | 463 | 394 | 423 | 421 ± 30 |
| | | Left | 434 | 463 | 429 | 516 | 461 ± 40 |
| DR4 | | Measurement Time | 17:15 | 16:40 | 17:50 | | |
| | | Right | 376 | 359 | 376 | | 370 ± 10 |
| | | Left | 376 | 382 | 388 | | 382 ± 6 |
| ORT1 | | Measurement Time | 17:00 | 17:25 | 17:00 | | |
| | | Right | 349 | 355 | 349 | | 351 ± 3 |
| | | Left | 349 | 360 | 355 | | 355 ± 6 |
| DR3 | | Measurement Time | 18:30 | 21:00 | 17:30 | | |
| | | Right | 277 | 260 | 272 | | 270 ± 9 |
| | | Left | 254 | 266 | 272 | | 264 ± 9 |
| DR5 | | Measurement Time | 16:30 | 16:40 | 18:30 | | |
| | | Right | 266 | 272 | 260 | | 266 ± 6 |
| | | Left | 318 | 300 | 318 | | 312 ± 10 |
| ORT5 | | Measurement Time | 17:00 | 16:30 | 16:40 | | |
| | | Right | 272 | 260 | 266 | | 266 ± 6 |
| | | Left | 324 | 324 | 355 | | 334 ± 18 |
| DR6 | | Measurement Time | 18:30 | 18:20 | 17:30 | | |
| | | Right | 216 | 219 | 192 | | 209 ± 15 |
| | | Left | 250 | 266 | 267 | | 261 ± 10 |
| DR7 | | Measurement Time | 18:00 | 17:45 | 17:30 | | |
| | | Right | 238 | 254 | 232 | | 241 ± 11 |
| | | Left | 535 | 456 | 477 | | 489 ± 41 |
| ORT9 | | Measurement Time | 17:10 | 17:40 | 17:00 | | |
| | | Right | 417 | 429 | 452 | | 433 ± 17.8 |
| | | Left | 307 | 318 | 324 | | 316 ± 8.62 |
| ORT3 | | Measurement Time | 16:30 | 16:15 | 16:50 | | |
| | | Right | 330 | 324 | 342 | | 332 ± 9 |
| | | Left | 423 | 429 | 388 | | 413 ± 22 |
| DR2 | | Measurement Time | 17:00 | 18:00 | 22:30 | | |
| | | Right | 202 | 185 | 203 | | 197 ± 10 |
| | | Left | 249 | 220 | 243 | | 237 ± 15 |
| ORT7 | | Measurement Time | 17:15 | 16:25 | 16:45 | | |
| | | Right | 260 | 266 | 260 | | 262 ± 3 |
| | | Left | 284 | 266 | 278 | | 276 ± 9 |

TABLE 4

| | | Average Fovea Choroidal Thickness (μm) | |
|---|---|---|---|
| ID No. | Age | Right | Left |
| ORT2 | 22 | 512 ± 21 | 462 ± 12 |
| ORT3 | 22 | 332 ± 9 | 413 ± 22 |
| ORT6 | 25 | 249 ± 18 | 288 ± 12 |
| ORT9 | 25 | 433 ± 17.8 | 316 ± 8.62 |
| ORT7 | 26 | 262 ± 3 | 276 ± 9 |
| ORT1 | 27 | 351 ± 3 | 355 ± 6 |
| ORT5 | 28 | 266 ± 6 | 334 ± 18 |
| DR4 | 30 | 370 ± 10 | 382 ± 6 |
| DR3 | 30 | 270 ± 9 | 264 ± 9 |
| DR1 | 35 | 410 ± 27 | 467 ± 28 |
| DR5 | 36 | 266 ± 6 | 312 ± 10 |
| DR7 | 41 | 241 ± 11 | 489 ± 41 |
| DR2 | 43 | 197 ± 10 | 237 ± 15 |
| DR6 | 48 | 209 ± 15 | 261 ± 10 |

TABLE 5

| | | Average Fovea Choroidal Thickness (μm) | |
|---|---|---|---|
| ID No. | Sex | Right | Left |
| DR4 | Male | 370 ± 10 | 382 ± 6 |
| DR5 | Male | 266 ± 6 | 312 ± 10 |
| DR2 | Male | 197 ± 10 | 237 ± 15 |
| DR3 | Male | 270 ± 9 | 264 ± 9 |
| DR7 | Male | 241 ± 11 | 489 ± 41 |
| DR6 | Male | 209 ± 15 | 261 ± 10 |
| | Average | 259 ± 57 | 324 ± 87 |
| ORT2 | Female | 512 ± 21 | 462 ± 12 |
| ORT3 | Female | 332 ± 9 | 413 ± 22 |
| DR1 | Female | 410 ± 27 | 467 ± 28 |
| ORT6 | Female | 249 ± 18 | 288 ± 12 |
| ORT1 | Female | 351 ± 3 | 355 ± 6 |
| ORT9 | Female | 433 ± 17.8 | 316 ± 8.62 |
| ORT5 | Female | 266 ± 6 | 334 ± 18 |
| ORT7 | Female | 262 ± 3 | 276 ± 9 |
| | Average | 352 ± 94 | 364 ± 75 |

INDUSTRIAL APPLICABILITY

The present invention can be used in all technical fields that require detection of a stressed condition, for the purpose of, for example, early detection of a stressed condition and prevention of diseases and symptoms induced by a stressed condition, and so on. In particular, the present invention is applicable to health management of workers, for example.

DESCRIPTION OF REFERENCE SIGNS

10: OCT Apparatus
11: Image Acquisition Unit
12: Input Unit
13: Computation Unit
13a: Image Signal Processing Unit
13b: Calculation Unit
14: Detection Unit
15: Storage Unit
16: Display Unit
X: Stress Detection Apparatus

The invention claimed is:

1. A method for detecting a stressed state, comprising a step of detecting a stressed state of a subject based on a tomographic image of a choroid of the subject, wherein the tomographic image includes a region including a position below a fovea of a retina, or a region including a position away from the fovea by a predetermined distance in a predetermined direction with respect to the fovea of the retina, the step of detecting a stressed state includes a step of detecting the stressed state of the subject based on a choroidal thickness at the position of the fovea of the retina, or the position away from the fovea by the predetermined distance in the predetermined direction with reference to the fovea of the retina, or based on a volume of the choroid calculated for a region centered around a position of the fovea of the retina, or the position away from the fovea by the predetermined distance in the predetermined direction with respect to the fovea of the retina, and the stressed state is detected when the calculated choroidal thickness or the calculated volume of the choroid is higher than a reference value calculated in advance from tomographic images of the choroids of healthy bodies that are not in a stressed state.

2. The method for detecting a stressed state according to claim 1, wherein a stressed state is detected when the calculated choroidal thickness is no less than 300 μm at a position below a fovea.

3. The method for detecting a stressed state according to claim 1, wherein the step of detecting a stressed state includes a step of correcting the calculated choroidal thickness based on at least one factor selected from among a detection time, the subject's age, sex, and history of present illness, and an indicator obtained from an eye structure.

4. The method for detecting a stressed state according to claim 3, wherein the step of detecting a stressed state includes a step of calculating a correction coefficient related to the choroidal thickness in an unstressed group based on a ratio of a standard choroidal thickness to the calculated choroidal thickness, the standard choroidal thickness being calculated from a group of which the at least one factor has a standard value, or related to the volume of the choroid in an unstressed group based on a ratio of a standard volume to the calculated volume, the standard volume of the choroid being calculated from a group of which the at least one factor has a standard value; and a step of correcting the choroidal thickness or the volume of the choroid using the correction coefficient to detect the stressed state of the subject.

5. The method for detecting a stressed state according to claim 1, wherein the step of detecting a stressed state includes a step of correcting the calculated volume of the choroid based on at least one factor selected from among a detection time, the subject's age, sex, and history of present illness, and an indicator obtained from an eye structure.

6. A stress detection apparatus (X) comprising:

an image acquisition unit (11) configured to acquire a tomographic image of a choroid of a subject;

a calculation unit (13b) configured to calculate a choroidal thickness or a volume of the choroid based on the tomographic image; and a detection unit (14) configured to detect a stressed state of the subject based on the choroidal thickness or the volume of the choroid, wherein the tomographic image includes a region including a position below a fovea of a retina, or a region including a position away from the fovea by a predetermined distance in a predetermined direction with respect to the fovea of the retina, and the detection unit (14) is configured to detect the stressed state of the subject based on a choroidal thickness at the position of the fovea of the retina, or the position away from the fovea by the predetermined distance in the predetermined direction with reference to the fovea of the retina, or based on a volume of the choroid calculated for a region centered around a position of the fovea of the retina, or the position away from the fovea by the predetermined distance in the predetermined direction with respect to the fovea of the retina, and the stressed state when the calculated choroidal thickness or the calculated volume of the choroid is higher than a reference value calculated in advance from tomographic images of the choroids of healthy bodies that are not in a stressed state.

7. The stress detection apparatus (X) according to claim 6, wherein the detection unit (14) is configured to calculate a correction coefficient related to the choroidal thickness in an unstressed group based on a ratio of a standard choroidal thickness to the calculated choroidal thickness, the standard choroidal thickness being calculated from a group of which at least one factor has a standard value, the at least one factor being selected from among a detection time, the subject's age, sex, and history of present illness, and an indicator obtained from an eye structure, or related to the volume of the choroid in an unstressed group based on a ratio of a standard volume to the calculated volume, the standard volume of the choroid being calculated from the group of which the at least one factor has a standard value; and correct the choroidal thickness or the volume of the choroid using the correction coefficient to detect the stressed state of the subject.

\* \* \* \* \*